United States Patent [19]

Turner et al.

[11] Patent Number: 5,424,963
[45] Date of Patent: Jun. 13, 1995

[54] MOLECULAR DYNAMICS SIMULATION METHOD AND APPARATUS

[75] Inventors: James D. Turner, Woburn; Hon M. Chu, Tewksbury; Paul K. Weiner, Somerville, all of Mass.

[73] Assignee: Photon Research Associates, Inc., San Diego, Calif.

[21] Appl. No.: 981,811

[22] Filed: Nov. 25, 1992

[51] Int. Cl.6 .............................................. G06F 15/60
[52] U.S. Cl. .................................... 364/578; 364/499
[58] Field of Search ................. 364/578, 499, DIG. 1, 364/232.1, 238.8, 149, 151, 806, DIG. 2, 931

[56] References Cited

U.S. PATENT DOCUMENTS

| | | | |
|---|---|---|---|
| T987,004 | 10/1979 | Feuer et al. | 364/DIG. 1 |
| 4,593,407 | 6/1986 | Konishi et al. | 364/DIG. 2 |
| 4,855,903 | 8/1989 | Carleton et al. | 364/DIG. 1 |
| 4,860,245 | 8/1989 | Kinoshita | 364/DIG. 2 |
| 4,908,781 | 3/1990 | Levinthal | 364/524 |
| 5,159,690 | 10/1992 | Margolus et al. | 364/DIG. 1 |

OTHER PUBLICATIONS

Margolus; "Cellular-Automata Supercomputers for Fluid-Dynamics Modelling", Physical Review 1986.
Sato et al; "Parallelization of Amber Molecular Dynamics Program"; IEEE 1992.
Kobayashi; "Modeling and Analysis"; Systems Programming Series 1981.
Wigner; "Parallel Processing and Computational Chemistry"; IEEE 1989.
Sayers "Symbolic Computer Language for Multibody Systems" J. Guidance Nov.–Dec. 1991, vol. 14, No. 6, pp. 1153–1163.
Sayers "Symbolic Vector/Dyadic Multibody Formalism for Tree-Topology Systems" J. Guidance Nov.–Dec. 1991, vol. 14, No. 6, pp. 1240–1250.
Jain et al. "Recursive Flexible Multibody System Dynamics Using Spatial Operators" Journal of Guidance, Control, and Dynamics Nov.–Dec. 1992, vol. 15, No. 6, pp. 1454–1466.
Frisch et al. "DNDISCOS—User & Programmers Manual" (Mar. 5, 1992).
Chun et al. "Discos Upgrade for Recursive Dynamics" The Center for Simulation and Design Optimization, The University of Iowa, (Feb. 1991).
Bodley et al. "A Digital Computer Program for the Dynamic Interaction Simulation of Controls and Structure (DISCOS)" NASA Technical Paper #1219, (1978) vol. 1.

*Primary Examiner*—Ellis B. Ramirez
*Attorney, Agent, or Firm*—Lappin & Kusmer

[57] ABSTRACT

A computer-assisted method for generating a dynamic model of a molecule is described based on information of the atomic structure. The model data is defined by rigid bodies corresponding to groups of atoms of the molecule with substantially no relative movement between the atoms, flexible bodies corresponding to groups of atoms which are characterized by relative movement between the atoms, and flexure elements which define an interconnection of two of the rigid bodies and the flexible bodies and predetermined degrees of freedom.

56 Claims, 16 Drawing Sheets

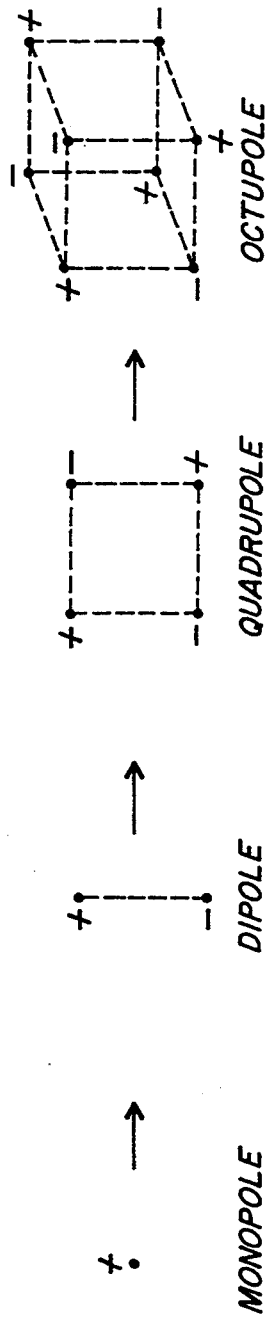

FIG. 7

MONOPOLE → DIPOLE → QUADRUPOLE → OCTUPOLE $$\phi = \phi^{(0)} + \phi^{(2)} + \phi^{(4)} + \phi^{(6)} + \ldots$$

WHERE $$\phi^{(0)} = \frac{q}{r}, \quad q = \sum_\alpha q_\alpha$$

$$\phi^{(2)} = \sum_\alpha q_\alpha \sum_i x'_{\alpha,i} \frac{\partial}{\partial x_i \partial x_j}\left(\frac{1}{r}\right)$$

$$\phi^{(4)} = \frac{1}{2}\sum_\alpha q_\alpha \sum_{ij} x'_{\alpha,i} x'_{\alpha,j} \frac{\partial^2}{\partial x_i \partial x_j}\left(\frac{1}{r}\right)$$

$$\phi^{(6)} = -\frac{1}{6}\sum_\alpha q_\alpha \sum_{ijk} x'_{\alpha,i} x'_{\alpha,j} x'_{\alpha,k} \frac{\partial^3}{\partial x_i \partial x_j \partial x_k}\left(\frac{1}{r}\right)$$

| MBO(N)D | | | | SHAKE | | | |
|---|---|---|---|---|---|---|---|
| Δt (fs) | TOTAL ENERGY | Phi | Psi | Δt (fs) | TOTAL ENERGY | Phi | Psi |
| 1.0 | 3.40 (.0012) | -75.35 (6.58) | 66.06 (8.86) | 0.5 | 3.48 (0.0144) | -75.56 (7.00) | 66.01 (8.93) |
| 2.0 | 3.38 (.037) | -75.31 (7.22) | 66.01 (8.96) | 1.0 | 3.33 (0.153) | -75.34 (7.20) | 66.11 (9.94) |

*FIG. 10*

| TIMESTEP SIZE (fs) | MEAN DEVIATION FROM AMBER RUN (Å)* | RMS DEVIATION OF TOTAL ENERGY OVER THE WHOLE RUN (%) | AMBER/MBO(N)D TIME RATIOS | |
|---|---|---|---|---|
| | | | NO INIT. TIME | WITH INIT. TIME |
| 2 | .03 | ** | 1.11 | 1.09 |
| 4 | .03 | ** | 2.23 | 2.15 |
| 8 | .03 | ** | 4.41 | 4.10 |
| 16 | .03 | 0.3 | 8.60 | 7.50 |
| 32 | .03 | 6.9 | 11.22 | 9.06 |
| 40 | .03 | 16.6 | 20.34 | 15.05 |
| 80 | .05 | 56.9 | 36.35 | 22.37 |
| 100 | .07 | 65.2 | 45.32 | 25.48 |
| 120 | .08 | 71.4 | 52.01 | 27.38 |

\* $\overline{\Delta x} = \frac{1}{N} \sum_{i}^{N} \Delta x_i$, WHERE $x_i$, WHERE $x_i$ = RMS DISPLACEMENT OF ATOM $i$.

\*\* LESS THAN 0.01 %

FIG. 13

| TYPE OF RUN | RMS FLUCTUATION (DEGREES) |
|---|---|
| AMBER | 17.55 |
| ONE FLEX BODY | 8.05 |
| THREE RIGID | 1.5 |
| FLEX (8) FLEX (4) FLEX (8) | 10.79 |
| FLEX.(2) PARTICLE FLEX (2) | 12.01 |
| FLEX (8) PARTICLE FLEX (8) | 18.18 |

*FIG. 16*

MOLECULAR DYNAMICS SIMULATION METHOD AND APPARATUS

A portion of the disclosure of this patent document contains material which is subject to copyright protection. The copyright owner has no objection to facsimile reproduction by anyone of the patent document or the patent disclosure, as it appears in the Patent and Trademark Office patent file or records, but otherwise reserves all copyright rights whatsoever.

FIELD OF THE INVENTION

The present invention is in the field of molecular dynamics simulation and more particularly is directed to computer implemented methods for modeling molecules.

BACKGROUND OF THE DISCLOSURE

Molecular dynamics (MD) simulations have been successfully applied over the past 15 years to study the structure, dynamics, and thermodynamics of complex molecular systems consisting of many thousands of atoms. Typical applications include: docking, diffusion, reaction pathway, phase transition, ant protein folding studies. Researchers in the pharmaceutical, polymer, and chemical industries are beginning to routinely use these techniques to design new drugs or materials.

User acceptance of these tools is based on the development of powerful computers and highly optimized commercially available dynamics software that can efficiently carry out the simulation of large solvated molecular systems. The traditional approaches to molecular dynamics are based on molecular mechanics or "force field" methods that use empirical approximations to compute the potential energy as a function of the Cartesian coordinates of the atoms of a molecule. An atomistic equation of motion (EOM) is derived for the molecule from Newton's third law, where the independent degrees of freedom (DOF) are defined by Cartesian coordinates. The forcing functions for the molecule are defined by gradients of the assumed potential energy terms that represent strain in internal coordinates (e.g., bonds, angles, and dihedral angles), as well nonbonded terms (e.g., hydrogen bonds, Van der Waal interactions and charge interactions).

The EOM has the form:

$$m_j \ddot{R}_j = F_j(R_1, \ldots, R_N); j = 1, \ldots, N_P$$

where $m_j$ denotes the mass of the j-th atom, $R_s = (x_s, y_s, z_s)$ denotes the positions vector for the s-th atom, $N_p$ denotes the number of atoms, and $F_j(*)$ denotes the position dependent sum of all the forces on the j-th particle. For small molecules, these equations are easily set up and solved. There are no approximations introduced other than those involved in setting up the empirical expressions and the parameter values used in defining the force field.

There are two sources of computational complexity for MD simulations. First, the energy function requires $N^2$ nonbonded interactions, where N is the number of atoms. This problem arises because every atom is affected by every other atom by way of long range interaction effects. For many applications the computation of the nonbonded interactions represent $\geq 90\%$ of the computer time.

Second, small integration step sizes must be used (i.e., 0.5 femtoseconds (fs)) in the integration of the EOM. The limitation in the size of the step size arises because of the following inequality:

$$\frac{P_{min(v)}}{\Delta t} \geq 2$$

where $P_{min(v)}$ denotes the period of the highest frequency response present in the system behavior and v denotes the wave-number. The high frequency motion must be eliminated in order to take larger step sizes.

In constrained dynamics approaches, constraints can be used to reduce the high frequency motion. Such constraints can be introduced into the atomic EOM by adding a force-like term consisting of the gradient of a position-dependent constraint equation times an unknown Lagrange Multiplier (LM), as follows:

$$m_j \ddot{R}_j = F_j(R_1, \ldots, R_N) + \sum_{r=1}^{N_o} \nabla_j C_r(R_1, \ldots, R_N) \lambda_r$$

subject to $$\nabla_j C_r(R_1, \ldots, R_N) \ddot{R}_j = 0;$$

$$j = 1, \ldots, N_p\ r = 1, \ldots, N_c$$

where $\nabla_j$ denotes the gradient with respect to the j-th atom position coordinates, $C_r(*)$ denotes the functional form the r-th constraint function, and $\lambda_r$ denotes the r-th LM. The solution for the LM is obtained by differentiating the gradient of the constraint equation and introducing the EOM. Straightforward manipulations lead to a LM solution defined by a linear matrix-vector algebraic equation of dimension $N_c \times N_c$, where $N_c$ denotes the number of constraints. As $N_c$ becomes large, the computational burden associated with the inversion matrix becomes prohibitive (e.g., $O(N^3)$).

There are two alternative classes of methods available for solving this problem. The first class of methods involves the construction of a set of generalized coordinates $$[M(q)]\ddot{q} = F(q, \dot{q})$$

where $[M(q)]$ denotes the $N \times N$ mass matrix, q denotes the generalized coordinate vector, and $F(*)$ denotes the force vector. This approach eliminates the constraint variables completely in the problem formulation. The generalized coordinate method is completely general. However, it requires the inversion of a $N \times N$ matrix $[M(q)]$, which is an $O(N^3)$ algorithm; that is, the inversion computation scales by the cube of the number of constraints imposed on the system. In addition, the equations are very cumbersome to implement and it is difficult to modify the equations once they are formulated.

Generalized coordinates have been used in MD for many years, though the applications have tended to be limited to short polymers (Pear et al. (1979) *J Chem Phys* 71:212; and Katz et al. (1979) *Comput Chem* 3:25). General-purpose formulations have not appeared previously for several reasons. First, classical analytical dynamics method, such as Lagrange's, involve the formulation of kinetic and potential energy expressions that require first and second partial derivatives with respect to the generalized coordinates (Ryckaert et al. (1985)

Mol Phys 55:549). This procedure is well defined but rapidly becomes unwieldy even for relatively low order problems (i.e., ≧30 independent variables).

The second class of methods involves calculating approximate solutions to the constrained EOM. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) easy to implement and scales as O(N) as the number of constraints increases. Therefore, the method is applicable to macromolecules. An alternative method, RATTLE (Anderson (1983) *J Comput Phys* 52:24) is based on the velocity version of the Verlet algorithm. Like SHAKE, RATTLE is an iterative algorithm.

Both of these approximate methods offer the ability to easily add bond constraints to a flexible system and allow a step size as large as 3-4 rs. However, adding any other types of constraints, even bond angle constraints, can greatly slow the convergence of SHAKE and limit the maximum step size.

Recent work has resulted in extensions of the SHAKE algorithm that allow for arbitrary geometrical constraints. The methods no longer have the convergence problems associated with the original SHAKE algorithm. These methods are also iterative and straightforward to implement. However, the maximum step size used appears to still be limited to about 3 rs. The systems used to test the methods were small (<50 atoms), and it is not clear how the methods would perform for larger systems with many thousands of constraints (Tobias et al. (1988) *J Chem Phys* 89:5115).

The shortcomings of these iterative methods are that they are not exact and that they are still limited to a relatively small step size. Even with the availability of supercomputers and highly optimized molecular dynamics packages, researchers are only able to observe relatively small atomic fluctuations that occur on the picosecond to nanosecond time scale. Longer time scale motion, such as helix motion, domain, and subunit motion, cannot yet be thoroughly looked at in detail with all atom simulations.

Most of the detailed studies of large molecule systems have involved approximations of the motion by using rigid bodies. Though it has been shown that these rigid body motions can sometimes dominate the atomic fluctuations, it cannot be known a priori that these approximations are valid. If the rigid groups are picked incorrectly the calculated motion will not represent reality. Even if the rigid groups are picked correctly, the barriers for motion between the groups will be artificially high because the atoms cannot make small displacements that will relieve much of the nonbonded repulsion.

To study large systems these motions, as well as even larger time scale motions, such as folding and unfolding transitions, a new class of dynamics algorithms is required that will reduce the degrees of freedom in a complex molecule system down to a manageable size, as well as scale up linearly for a complex system so that protein conformational changes can be studied at any desired level of detail.

Accordingly, is an object of the present invention to provide an improved method for simulating the dynamics of molecules.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 7 illustrates a multipole expansion method for evaluating the energy potential of long-range electrostatic field contributions.

FIG. 10 summarizes the results of two dynamic simulations on a glycine dipeptide using either MBO(N)D or AMBER.

FIG. 13 compares dynamic simulations on decaglycine performed by MBO(N)D (20 modes) and AMBER.

FIG. 16 compares the RMS fluctuations of the angle between 2 helix lobes during dynamic simulations performed by AMBER and MBO(N)D.

SUMMARY OF THE INVENTION

Figure 1:
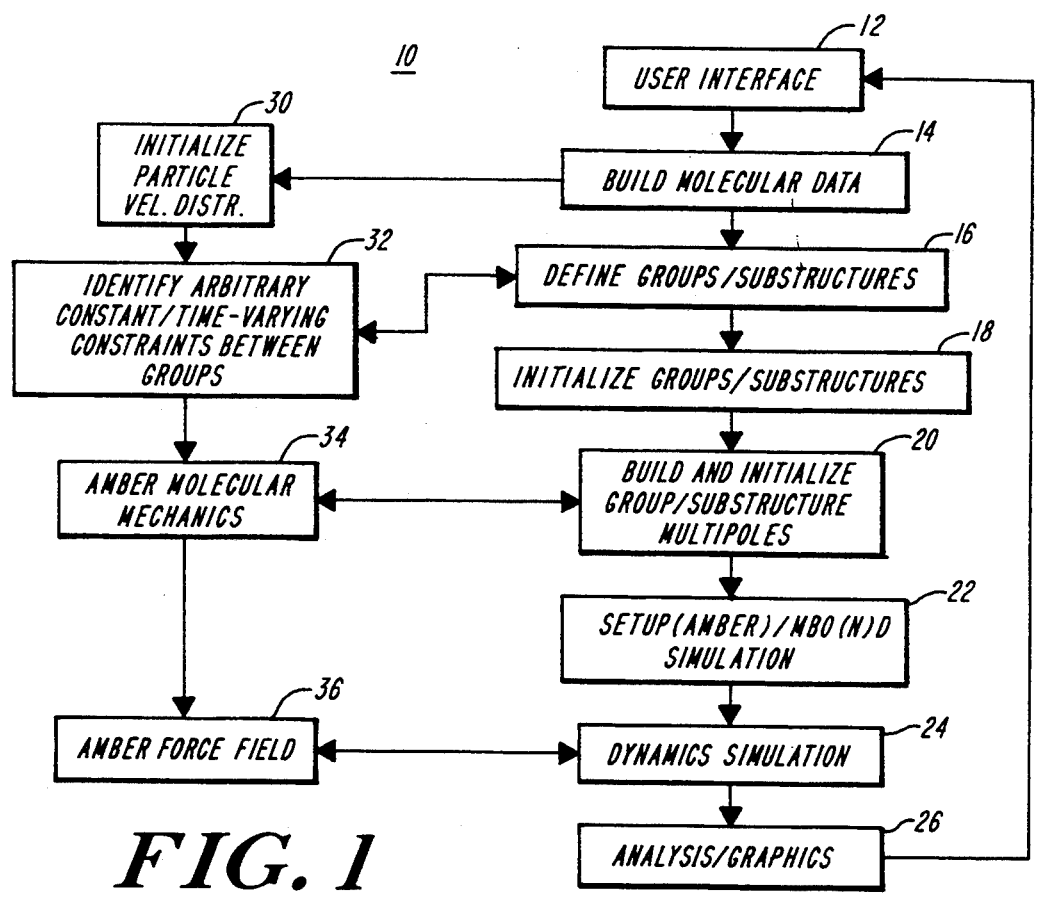
FIG. 1 shows exemplary steps of a computer-implemented method of generating a dynamic model of a molecule in accordance with the invention.

Briefly, the invention is a computer-assisted method for generating a dynamic model of a molecule by partitioning the molecule into interconnected bodies, developing the equations of motion using Lagrange multipliers to maintain prescribed constraints on the hinges between the bodies, and recursively solving the equations of motion for the absolute position and velocity of each of the bodies.

From a predetermined atomic structure, model data for the molecule is generated by partitioning the molecule into rigid bodies and flexible bodies. Rigid bodies correspond to groups of one or more atoms characterizesd by substantially no relative movement therebetween. Flexible bodies correspond to groups of two or more atoms of the molecule are characterized by relative movement therebetween. Each body is interconnected being defined by a flexure element and having predetermined degrees of freedom. Position coordinates and velocities of the atoms of the molecule are measured with respect to a reference coordinate system, and in the instance of flexible bodies, vibrational modes of motion of the flexible are calculated. This first and second base data is then processed to a local coordinate system assigned to each body. For both rigid bodies and flexible, a local coordinate system is identified, and the position, velocity and acceleration of each atom of the body is determined relative to the local coordinate system. In the case of flexible bodies, at least one modal amplitude and modal rate associated with the body is also determined.

Hinge constraints are calculated between adjacent bodies, and are defined with respect to the local coordinate system of each of the adjacent bodies, and further includes a component of a vector $\{\beta\}$ which is representative of all of the bodies. From the hinge constraints, hinge rates corresponding to $$\frac{d}{dt}\{\beta\}(=\{\dot{\beta}\})$$

and hinge accelerations corresponding to $$\frac{d}{dt}\{\dot{\beta}\}(=\{\ddot{\beta}\})$$

are determined.

Equations of motion are generated for each of the bodies in the system, and take on the form $U=[M[^{-1}G+B\lambda]$, where U is representative of the absolute acceleration of a body; [M] is representative of the mass of the body; G is representative of the generalized force vector of the body; B is representative of the constraint kinematic coefficient matrix for the body; and $\lambda$ is a Lagrange multiplier for the hinge constraints of the body. The equations of motion developed for each body define a vector $\{\ddot{U}_i\}$, where i is an index representative of the body.

The equations of motion are recursively solved to determine the absolute position and velocity of each body from $\{U_i\}$. In one aspect of this invention, the recursive solution of the equations of motion includes the implementation of an O(N) procedure. For instance, a tree topology can be defined for the bodies of the partitioned molecule, with one body being defined as the base body. In considering the base body, a hinge constraint component is associated with the base body and inertial space. The base body is additionally associated with at least one other hinge constraint component of vector $\{\beta\}$ associated with adjacent bodies. The remaining bodies of the molecule are classified as intermediate bodies when associated with hinge constraint components associated with at least two other bodies; or as end bodies in the tree topology when associated with hinge constraint components associated with only one other body. The absolute rate of the base body with respect to inertial space is determined for the base body. Then in a first forward sweep starting with the base body and progressing serially outward on the tree topology, the absolute rate and absolute acceleration associated with each body is determined from the hinge rate, modal amplitude rate and absolute rate of the next body inboard on the tree topology. (i.e. first solve for body 1, then solve for body 2 in terms of body 1, then body 3 in terms of body 2, and so on out to body N). Then in a backwards sweep starting with the end bodies of the structure and proceeding inward to the base body, the inertia and generalized forces associated with each body are determined from $\{\ddot{U}_i\}$ and $\{\ddot{\beta}\}$ of the next outboard body (i.e. starting with body N, specify the force and torque parameters of N-1 in terms of N, N-2 in terms of N-1, and so on in to the base body). In second forward sweep starting with base body and working serially outward, the relative hinge accelerations and relative modal accelerations of each body are determined from the hinge acceleration and modal acceleration of the next inboard body.

DESCRIPTION OF THE PREFERRED EMBODIMENT

The present invention is a computer-implemented method for generating a dynamic model of a molecule. A preferred form of the method is shown in FIG. 1. In that figure, a user operates a programmed digital computer which initiates and controls operation of the method 10 of the invention (via user interface 10) by initially generating molecular data (block 14), followed by defining groups or substructures for the molecule (block 16), initializing the position and velocity for the defined groups or substructures (block 18), building and initializing group or substructure multipoles (block 20), setting up the multiple body Order (N) dynamics (block 22), performing dynamics simulation computations (block 24) and analyzing and displaying the simulation results (block 26). In support of these substeps, following generation of the molecular data (block 14), and responsive to the definition of groups or subgroups (block 16), the computer performs the substeps of initializing the particle velocity distribution (block 30) followed by identifying fixed and/or time-varying constraints between groups (block 32) and performing molecular mechanics computation (block 34) and force field computations (block 36).

Figure 2:
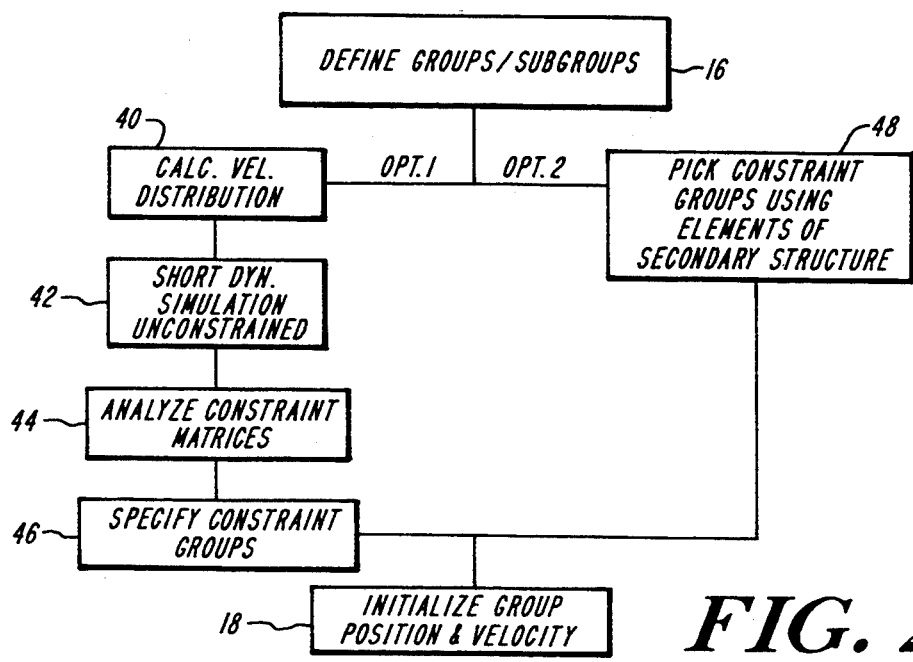
FIG. 2 shows exemplary substeps of the define group substep of the method of FIG. 1.

As described more fully below, the define group or substructure substeps (block 16) can, in the preferred form of the invention, follow either of the optional substep paths shown in FIG. 2 (option 1: blocks 40, 42, 44, and 45; option 2: block 48).

Figure 3:
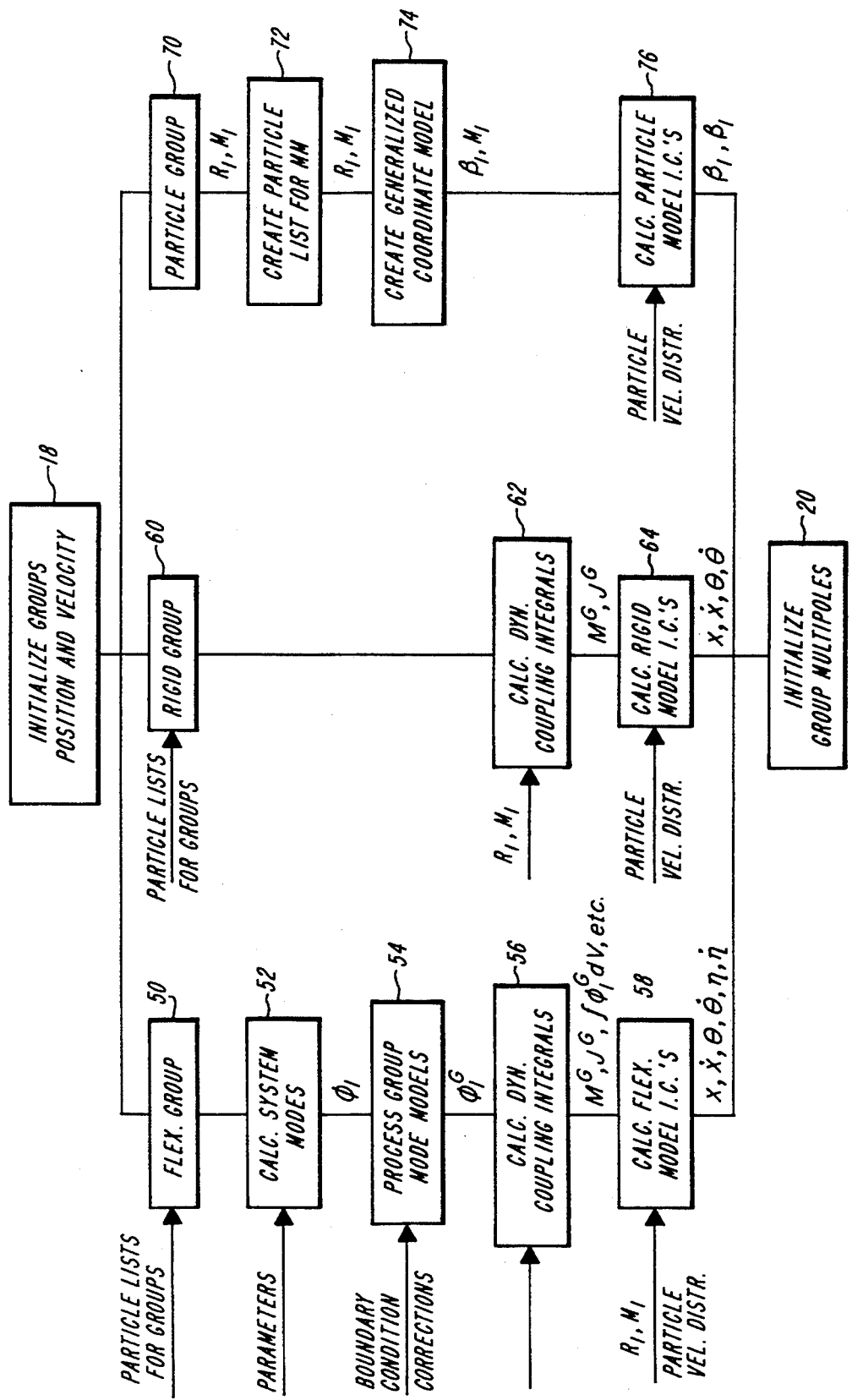
FIG. 3 shows exemplary substeps of the initialize group substep of the method of FIG. 1.

The detailed substeps of the initialize group position and velocity substep (block 18) are shown in FIG. 3 and include separate substep paths for flexible body groups (blocks 50, 52, 54, 56, 58), rigid body group (blocks 60, 62, 64) and particle groups (blocks 70, 72 and 74).

Figure 4:
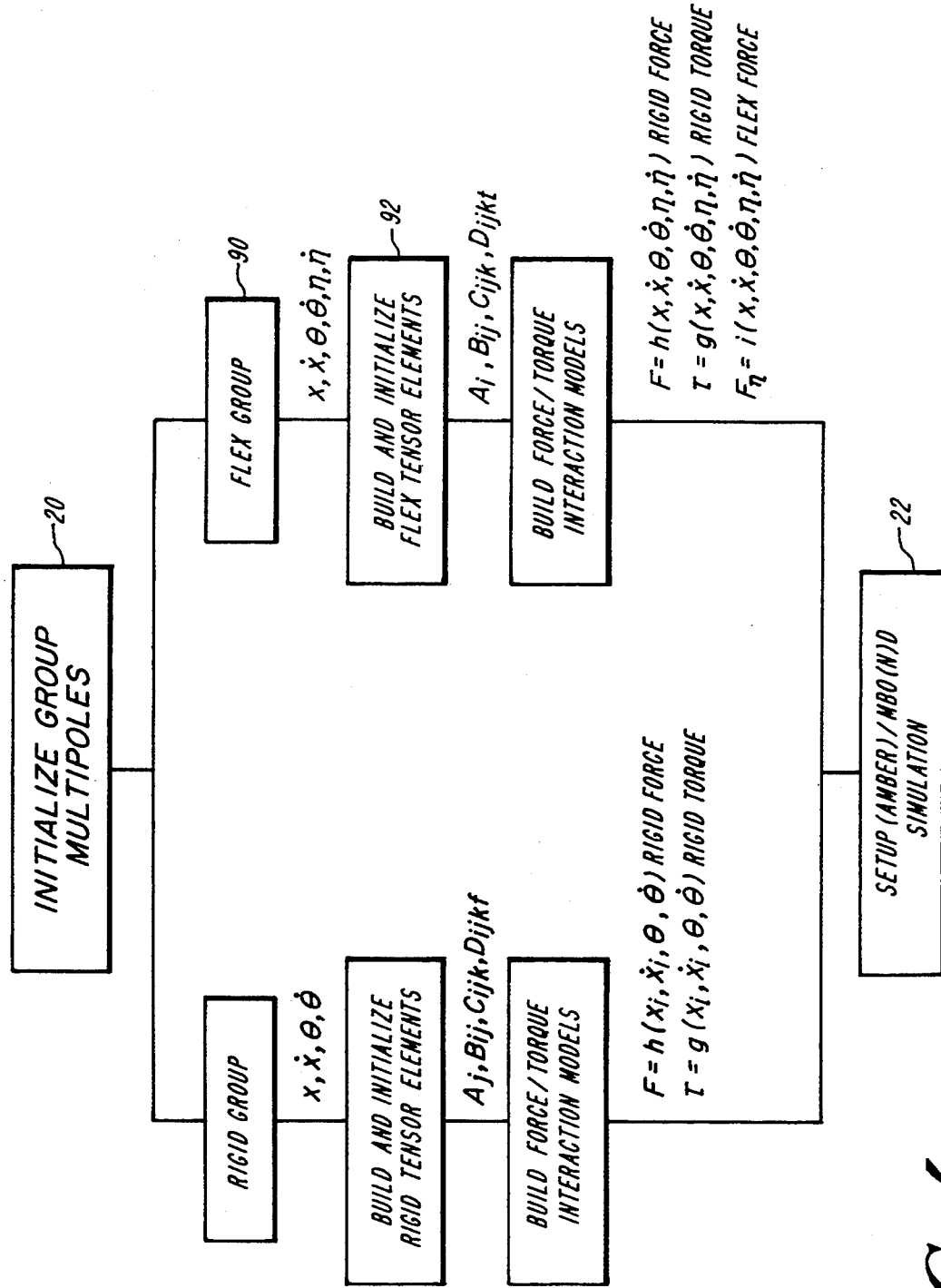
FIG. 4 shows exemplary substeps of the initialize group multipoles substep of the method of FIG. 1.

The detailed substeps of the initialize group multipoles substep (block 20) are shown in FIG. 4 and include separate substep paths for rigid groups (blocks 80, 82, 84) and flexible groups (blocks 90, 92, 94).

Figure 5:
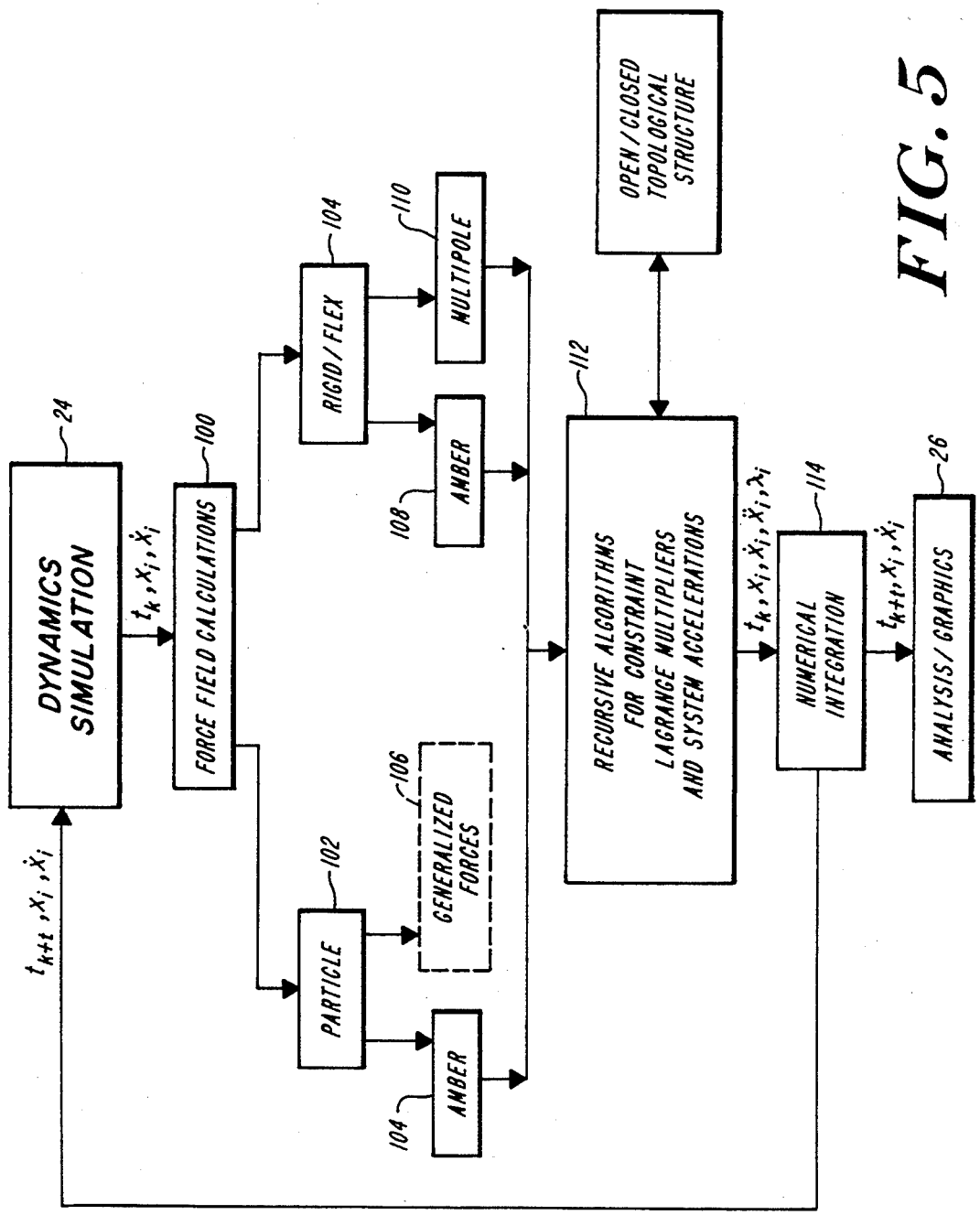
FIG. 5 shows exemplary substeps of the dynamics simulation substep of the method of FIG. 1.

The detailed substeps of the dynamics simulation (block 24) are shown in FIG. 5 and include force field calculations (block 100) for particles (block 102) and for rigid and flexible groups (block 104). For particle groups, those calculations are performed using techniques of Assisted Model Building and Energy Refinement (Amber Systems Inc, Cambridge, Mass.) referred to as AMBER (block 104) and in view of generalized forces, forces described in terms of generalized variables, (block 106). For rigid and flexible groups, those calculations are performed using AMBER (block 108) and multipole calculations (block 110). The equations of motion (EOM) for the molecule are established using the results of the force field calculations, and the molecular dynamics are determined by applying a recursive algorithm to determine Lagrange Multipliers for the system and the system ascceler ations (block 112). Then, the EOM are numerically integrated (block 114) to generate data representations of the position and velocity of each atom in the molecule. The recursive algorithm step is applied over open or closed topological structures (block 118). The resultant data is analyzed and/or displayed (block 26), as required by the user.

This invention addresses several computational bottlenecks that have limited the utility of molecular simulations. These critical limiting factors include the time required to evaluate the energy function, and the computational resources required to carry out meaningful simulations that can be compared with experiment. To overcome these limitations, this invention includes one or more of the following technologies: partitioning strategies, multipole expansions, and recursive algorithms.

Partitioning strategies allow the user to define or model the motions of collections of atoms in terms of particles, rigid bodies, and flexible bodies, where in some forms of the invention, particles can be considered a degenerate case of a rigid body. This approach is enabled by using multibody dynamics techniques that permit large bodies to be broken into many smaller bodies that can undergo large and rapid relative motions. The partitioning strategies use exact methods that approximately retain the physical rigor of the exact method. This approach provides benefits which include significant reduction in the number of degrees of freedom (DOF) that must be retained in the model and simplification of the potential surface, thereby allowing more rapid exploration of the phase space motions.

Multipole expansions permit a significant reduction of the time required to compute the $O(N^2)$ electrostatic terms. In the prior art, the evaluation of these terms typically takes 90% of the time required for the determination of the energy function. The multipole expansion replaces the static collection of N charges with M power series expansions where $M<<N$. By carrying out each expansion to a high enough order, the results are quantitatively similar to the exact calculations.

A recursive dynamics formulation permits the efficient processing of the constraints generated by the partitioning and body modeling strategies. The traditional approach for handling $N_c$ constraints requires either the inversion of an $N_c \times N_c$ matrix or obtaining an approximate solution through an iterative procedure. The recursive formulation of the present invention reformulates the large matrix problem into a series of many small matrix problems. This method uses no approximations and retains the exact physics of the system. For example, a 350 body problem with 1750 constraints would traditionally require the inversion of a $1750 \times 1750$ matrix. The method of the present invention only requires the inversion of $5 \times 5$ matrices and subsequently is $2535 \times$ faster than the traditional method in the 350 body system.

The advantages of the approach of the present invention include: 1) The constraints are solved exactly at each time step, 2) The solution procedure is noniterative, 3) The method is recursive and scales as O(N), 4) The method is very stable numerically, 5) The method is very amenable to parallel processing, 6) Both fixed and time-varying constraints can be handled, and 7) Fewer DOF are retained in the EOM's. The stability of this method, termed "MBO(N)D" for Multiple Body Order(N) Dynamics, permits use of a much larger integration step size that can be used with prior art techniques, thereby minimizing the number of force field evaluations required during the integration of the EOM's.

In MBO(N)D, the basic mathematical description of the coupled system dynamics is defined by invoking the use of Lagrange's method. In this approach, the molecule is partitioned into bodies, and each body is modeled independently in inertial space in terms of generalized coordinates which characterize the rigid body rotations and translations and flexible body deformations. The equations of motion are developed in a completely general way for a single body. After the equations of motion are obtained, coordinate transformations are introduced which replace the independent generalized coordinates with quasi-cooridinates. The quasi-coordinates replace the inertial frame description of the motion with a body frame description of the motion, where the body frame is a dynamic reference frame which moves with the body. The overall system-level motions (i.e. of the entire molecule) are developed by imposing velocity constraints at the interconnection points between contiguous bodies. As a result, each hinge can have between 0 and 6 degrees-of-freedom (DOF) for describing the relative motion between bodies. Because constraints are imposed on the system-level motion, the mathematical description of the motion contains redundant DOF. The redundant DOF are handled by introducing Lagrange multipliers for maintaining the velocity constraints imposed at the constrained hinge DOF. An algebraic solution method is used to compute the Lagrange multipliers for each calculation of the system acceleration. The method of the invention will now be described in terms of the subsystem of pre-processing of data, partitioning, mapping of coordinates to a body frame of reference, establishing equations of motion and solving equations of motion.

I. Preprocessing of Data

Before considering the dynamics of the molecule to be studied, the structure of the molecule and velocities of each atom are calculated at a simulation temperature ($T_o$) at which the dynamics simulation is to be determined. Computer programs for performing energy minimization routines are commonly used to generate molecular models. At the heart of these programs is a set of subroutines that, given the position of every atom in the model, calculate the total potential energy of the system and the force on each atom. These programs may utilize a starting set of atomic coordinates, such as obtained by X-ray crystallography or any other set of model coordinates, the parameters for the various terms of the potential energy function, and a description of the molecular topology (the covalent structure). Since the various covalent interactions are often expressed in terms of the internal coordinates (bonds, bond angles, and torsions), the covalent structure may be specified by identifying the pairs of atoms in all bonds, triplets of atoms defining the bond angles, and quartets of atoms defining torsional rotations about bonds. Common features of molecular modeling methods include: provisions for handling hydrogen bonds and other constraint forces; the use of periodic boundary conditions; and provisions for occassionally adjusting positions, velocities, or other parameters in order to maintain or change temperature, pressure, volume, forces of constraint, or other externally controlled conditions.

Most conventional energy minimization methods use the input data described above and the fact that the potential energy function is an explicit, differentiable function of cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules such as peptides, proteins, nucleic acids, polymers and zeolites.

In general, energy minimization methods can be carried out for a given temperature, $T_i$, which may be different than the dynamics simulation temperature, $T_o$. Upon energy minimization of the molecule at $T_i$, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at $T_i$, the system is "heated" or "cooled" to the simulation temperature, $T_o$, by carrying out an equilibration run where the velocities of the atoms are scaled in a step-wise manner until the desired temperature, $T_o$, is reached. The system is further equilibrated for a specified period of time until certain properties of the system, such as average kinetic energy, remain constant. The coordinates and velocities of each atom are then obtained from the equilibrated system.

II. Partitioning

Before the dynamics simulation can be carried out, the molecular model must be partitioned into two or more bodies which are connected by hinge elements. The bodies can be defined as rigid bodies, flexible bodies or particles, where in some forms of the invention, particles are considered to be a degenerate case of a general multiparticle rigid body. The partitioning can be carried out at some point during the modeling and energy minimization preprocessing of the data, and is preferably accomplished after the system has been equilibrated at $T_o$. The boundaries defining each body can be determined by structural considerations such a secondary structure elements or domain structures. By way of example, an α-helical segment of a protein can be defined as a body. Alternatively, an entire domain of a protein can be defined as a body.

The bodies can also be defined from other intrinsic observations about the moledule, such as correlated motion between groups or atoms that are derived by analyzing the results of a short (tens of picoseconds) simulation performed on the system with few or no constraints (perhaps only bond constraints). FIG. 2 illustrates by way of a block diagram two possible paths useful in partitioning a molecule. Option 1 demonstrates the use of analyzing the correlation of motion between atoms or groups of atoms to define a body. Alternatively, Option 2 defines a body from knowledge of secondary structure information obtained from the initial structure. In determining whether a given collection of atoms assigned to a body constitute a rigid body or a flexible body, the degree of relative motion between the atoms of the collection is analyzed. Rigid bodies can be defined as a collection of atoms which exhibit a level of relative motion to one another that is below a predetermined threshold value, while flexible bodies exhibit relative atomic motion above the predetermined threshold value.

In evaluating the relativie motion of atoms within a body, the "breathing" modes calculated from the normal mode analysis can be used. The predetermined threshold value can be set, for instance, by establishing a modal amplitude cut-off value across a given vibrational frequency range. By way of example, for many macromolecules, a user can include all modes with wavelengths $<75$ cm$^{-1}$, as this range is well known to include the dominant low frequency breathing modes of large molecules. As used herein, atoms of a given body are said to have substantially no relative movement there between if the peak amplitude of the modal motion or the normal mode momentum contribution are below the predetermined threshold value. It is therefore clear that semi-rigid bodies can be defined as rigid bodies or flexible bodies, depending on vibrational frequencies examined and the threshold value selected.

Where atoms cannot be conveniently grouped into either a rigid body or a flexible body because the predicted motion of that atom would exceed the range of validity of that assumed in the modal approximation, such as would occur in a group of atoms undergoing a conformational transition or enen atoms in a flexible loop of a protion, each ungrouped atom can be assigned as a particle, which is attached to other bodies by hinge elements. Alternatively, the ungrouped atom can be considered as a single atom rigid body.

III. Mapping Coordinates to Body Frame

After partitioning the molecule into bodies, the inertial frame coordinates of the bodies are replaced with quasi-coordinates which describe the motion of each body relative to a respective body frame, where the body frame is a dynamic reference which moves with a given body. For each body structure, a reference point is selected to be the origin of the body frame. This point can be arbitrarily selected relative to the body to which it is attached, but is preferably an atom of the body or the center of mass of the body. The position, motion and velocity of each atom of the body are computed relative to the reference point of that body. As described below, in the body frame, these attributes are described in the body constraint equations for rigid, flexible and particle bodies in terms of translational and rotational variables. In this manner, the linear and angular momentums calculated in the modeling step are conserved when mapped onto a body reference frame.

A typical flexible body requires both mass and modal data that reflect a coordinate system that is consistent with the body axis reference system for that body. For the flexible bodies, the normal modes of the system can be ported to the body reference frame of flexible bodies. The modal coupling approach for establishing modal properties for a given flexible body can use the same reference body axis system. This can be accomplished by including in the constraint equations for flexible bodies, modal amplitude (i.e. body deformation) terms. To establish these equations, the global mode shapes calculated in the modeling step are processed to local mode shapes. To increase calculation speed, the user can define a bandwidth of meaningful vibrations (i.e. restrict the number of degrees of freedom for breathing) to be carried through the dynamics simulation and drop out those vibrational modes with small amplitudes and/or at frequencies which do not significantly effect the overall dynamics of the molecule. It has been observed that, particularly for larger order systems, only a few local normal modes are required to model global behavior of the molecule.

Figure 6:
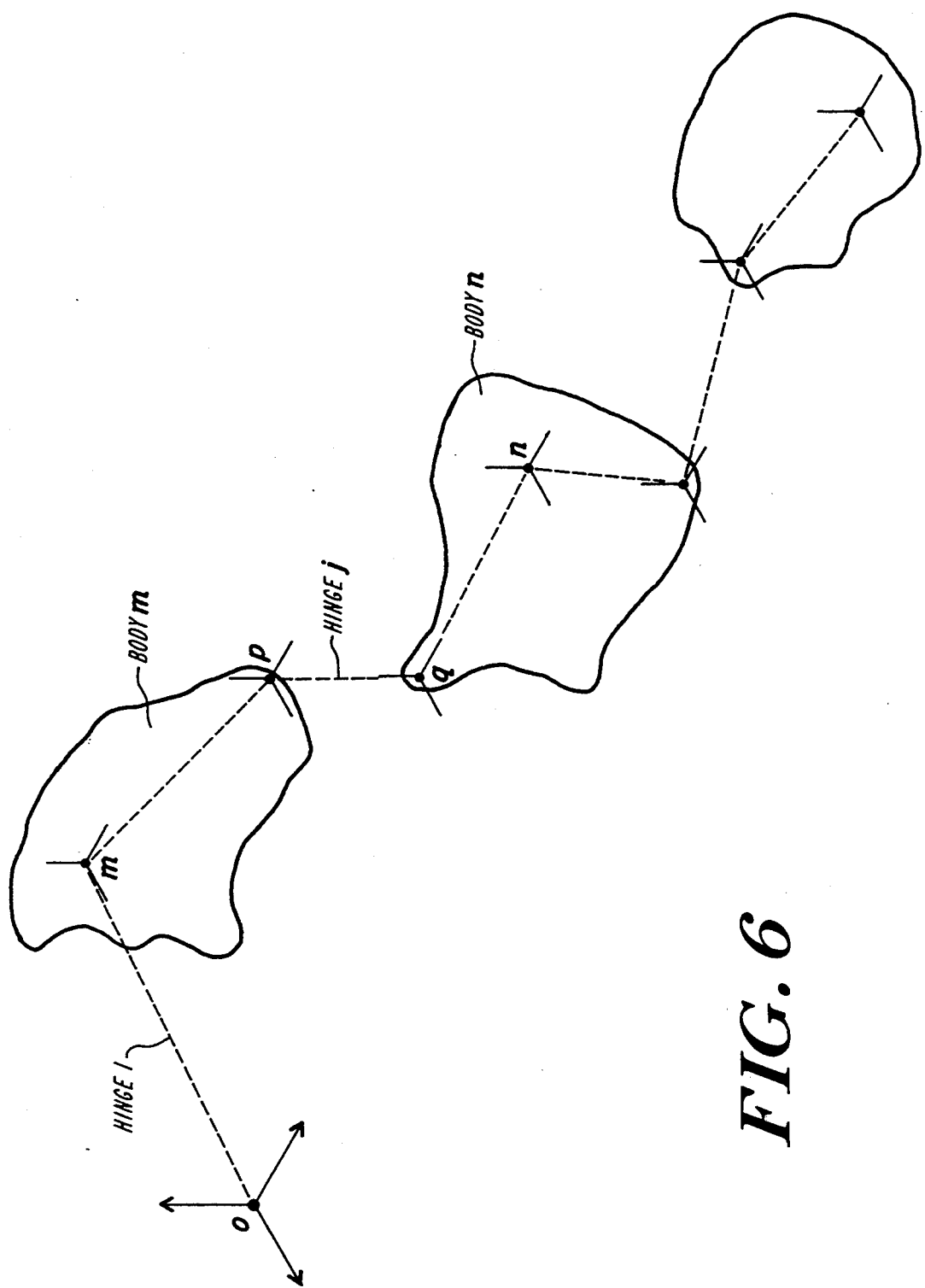
FIG. 6 shows a contiguous system of bodies and hinges, including hinge 1 between the base body and the inertial reference frame.

The coupling between a pair of adjacent bodies is referred to as a hinge. A hinge defines the constraints between a point on one body, and a point on the other body of the pair. Referring to FIG. 6, point p and point q comprise the end points of a hinge. A typical body may contain one or more hinge parts, but a hinge may be associated with only two bodies. Hinge 1 is given special consideration. It is also a pair of points, but one of the pair is coincident with the reference point of the base body (body as in FIG. 6), and the other point of the pair is coincident with the inertial origin. Thus, motion "across the hinges" is used to represent system motion. The reference point of the base body is located with respect to the inertial origin by an inertially referenced position vector. The attitude of the reference frame of the base body, with respect to the inertial frame, is represented by three Euler angles. Thus, six position/attitude coordinates are associated with hinge 1.

Each of the remaining hinges is considered in a manner somewhat similar to that of hinge 1. Referring to FIG. 6, it is noted that there is an orthogonal reference frame attached to hinge point p and another to hinge point q. The triad of point p may have a "natural" (or undeformed) misalignment with respect to the triad of body m, plus additional nonalignment caused by elastic deformation if body m is flexible. The same relationship is true concerning points n and q. Motion of the q frame on body n is measured relative to the p frame on body n, and the p and q frame are positioned with respect to body m and n reference axis systems. In this manner, the bodies of the system are connected through a set of hinges.

Six relative positional/attitude coordinates are associated with the hinge of point q and p. Point q is located from point p with a p-frame reference position vector. The attitude of the q-frame, with respect to the p-frame, is represented by three Euler rotations. In the case of flexible bodies, if $N_H$ is the number of system hinges, 633 $N_H$ position coordinates are used in conjunction with modal displacement coordinates for defining the system's position state. All necessary kinematic information pertinent to the hinge is obtained through expressing the velocity of point q relative to point p, and in expressing the relative angular velocity between the q- and p- frames. It is convenient that the angular velocity components are projections onto skew axes (Euler angle rates) and that translational velocity components are projections onto the axes of the p-triad. Furthermore, it is clear though that the "hinge" between two continguous bodies may actually permit relative translational motion of the two bodies at the hinge.

It is also noted that for all bodies, only the time-variable position coordinates of the 6×NH set of candidates are considered as state-vector elements. The position coordinates whose rates are constrained to zero are not included, but the position coordinates themselves need not be zero.

IV. Deriving the Equations of Motion

Having modeled the molecule as a dynamic system of interconnected rigid and flexible bodies, the unabridged nonlinear equations of motion are determined for the system, either nonlinear or linearized versions of the time-domain solutions are solved to describe the acceleration, velocity and positional coordinates over time for the molecule. The differential equations of motion, and auxiliary equations that characterize the molecule, may take on any one of several equivalent forms. Equivalent form means that the same physical system can be characterized by more than one set of mathematical variables, though either a minimum set or a redundant set of variables must be used. For example, the motion equations can be derived using Lagrange's equations, or alternatively, from the Newton-Euler equations. Clearly, the methods are equivalent if they are developed through completion without any compromising simplifications.

Equations of motion are any dynamical system derived, in one way or another, from considerations of equilibrium where a system of impressed force may or may not be present, that lead to the system expressing an acceleration. The equations of motion are given generally as $\{P\}=\{G\}$, where $\{P\}$ represents a column vector of ordinary momemnta, and $\{G\}$ represents a collection of all external and internal forces. In developing the equations of motion, it is well known that it is possible to account for all state dependent and explicitly time dependent effects in an unabridged system.

The preferred method of solution of the equations of motion will now be described in detail. In a particular embodiment described below, the formulation and numerical implementation of motion equations for the system of interconnected bodies involves a vector of Lagrange multipliers, $\{\lambda\}$. The equations of motion are developed using Lagrange's equations, including in the formulations auxiliary nonholonomic, rheonomic conditions of constraint. Lagrange multipliers are used as interaction forces to maintain prescribed constraints. Nonlinear flexible/rigid dynamic coupling effects are accounted for in unabridged fashion for individual bodies and for the total system. Elastic deformations can be represented by normal vibrational modes or by any adequate series of Ragleigh functions, including so-called quasi-static displacement functions. The traditional numerical solution of the Lagrange Multipliers is defined by a linear system of equations, where the matrix dimension is defined by the number of system-level constraints that have been imposed on the motion. As more bodies are simulated, the number of constraints increases rapidly. As a practical matter, this modeling approach is generally limited to modeling less than 15 bodies. With the new methods described below, the computational burden is reduced from $O(N^3)$ to $O(N)$, where N is the number of bodies being modeled. This new method effectively permits problems of arbitrary size to be formulated and efficiently solved.

The equations of motion for the $j^{th}$ body of the system can thus be extended to include the effective generalized forces on the molecule by expressing the equations of motion in the following state space form:

$$\{\dot{U}_j\} = [M_j^{-1}](\{G_j\} + [b_j^T]\{\lambda\}) \tag{1}$$

The required kinematic and selection transformations, and the additional controller equations collected together are:

$$\{\dot{\xi}_j\} = [S_{\xi j}]\{U_j\} \tag{2}$$

$$\{\dot{\beta}\} = \sum_j [B_j]\{U_j\} \tag{3}$$

$$\{\dot{\delta}\} = f(\{\beta\},\{\dot{\beta}\},\}\xi\},\{\dot{\xi}\},\{\delta\}) \tag{4}$$

subject to the hinge constraint equations $$\sum_j [b_j]\{U_j\} = \{a\} \tag{5}$$

Equation (1) defines the constrained acceleration equation of motion for the j-th body for $j=1, \ldots, N_b$, where $[M_j]$ is the mass matrix; $\{G_j\}$ is the generalized force vector which represents a collection of all external forces, internal forces and dissipative forces, which can comprise body forces, torque, generalized modal force vectors, elastic restoring forces, and damping forces, $\{\lambda\}$ is the system-level Lagrange multiplier vector for the hinge constraints; $N_b$ is the number of bodies; and $\{U_j\}$ is the j-th body velocity state. The components of $\{U_j\}$ are defined as follows:

$$\{U_j\} = \{\omega_x\, \omega_y\, \omega_z\, u\, v\, w\, \dot{\xi}_1 \ldots \dot{\xi}_N\}_j^T$$
$$= \{\gamma_j \dot{\xi}_j\}^T$$

where $\omega x$, $\omega y$, $\omega z$ are j-th body quasi-coordinate components of the angular velocity vector, u, v, w are the j-th body quasi-coordinate components of the translational velocity vector, $\{\gamma\}$ is a $6 \times 1$ vector which combines both the angular velocity and translational velocity components, $\dot{\xi}_1, .\dot{\xi}, . \dot{\xi}_N$ are the j-th body deflection coordinate time derivatives, and N is the number of deflection coordinates for the j-th body. In Eqn. (2) the $[S_{\xi j}]$ matrix represents a selection operator for retrieving the deflection coordinate time derivative from $\{U_j\}$. The $\{\beta\}$ vector in Eqns. (3) and (4) represents the independent generalized coordinates used for tracking the motion of all the bodies being simulated (i.e. gimbal angles and cartesian position vector components). In Eqn. (3) the $[B_j]$ matrix represents a kinematic coefficient matrix that transforms the quasi-coordinates and defelection coordinates of $\{U_j\}$ into independent velocity coordinates and is of very similar form to the $[b_j]$ of Eqn. (1). The collection of $\{\dot{\xi}_j\}$ and $\{\gamma_j\}$ vectors, for the n bodies, and the $\{\beta\}$ vector are truely the generalized coordinates of the structural system as they provided complete configuration description of the system bodies.

To complete the definition of the state equations, additional differential equations, such as those linking diffusional drag forces to state elements (attitudes, their rates and time integrals) through an appropriate control law. The $\{\delta\}$ vector in Eqn. (4) represents the user-defined control variables, thermal variables, or other variables required for completely specifying the problem-dependent environment of each simulation application. There are a large variety of additional differential equations a user may desire to include. The functional dependence of $\{\delta\}$ on state vector elements is not restricted to linear form. In fact, the additional differential equations may include sample data systems, dead bands, and any other type nonlinearity or discontinuity that can be numerically represented.

In order to numerically evaluate $\{\lambda\}$, time derivatives of kinematic coefficients (velocity transformations) associated with hinges must be calculated. Therefore, before Eqns. (1) through (4) can be solved for the constrained system accelerations, the Lagrange multiplier vector, $\{\lambda\}$, of Eqn. (1) is evaluated subject to satisfying the hinge constraint conditions defined by Eqn. (5). The $\{a\}$ is a $N_c \times 1$ vector representing the user-specified constrained hinge rates where $N_c$ denotes the number of hinge constraints. The solution for $\{\lambda\}$ is obtained by a three-step process.

The first step consists of differentiating Eqn. (5), leading to $$\sum_j ([\dot{b}_j]\{U_j\} + [b_j]\{\dot{U}_j\}) = \{\dot{a}\} \tag{6}$$

Second, introducing the $\{\dot{U}_j\}$ vector from Eqn. (1) into Eqn. (6), to obtain $$\sum_j ([\dot{b}_j]\{U_j\} + [b_j][M_j^{-1}](\{G_j\} + [b_j^T]\{\lambda\})) = \{\dot{a}\} \tag{7}$$

Third, Eqn (7) is solved as an algebraic equation for $\{\lambda\}$, yielding $$\{\lambda\} = [A^{-1}]\{\mu\} \tag{8}$$

where $$[A] = \sum_j [b_j][M_j - 1][b_j^T]$$

$$\{\mu\} = \{\dot{a}\} - \sum_j ([\dot{b}_j]\{U_j\} + [b_j][M_j^{-1}]\{G_j\})$$

With Eqn. (8), the constrained equations of motion defined by Eqn. (1) can be numerically evaluated. The equations of motion are defined at the body level. The Lagrange multipliers, however, are computed for all the constraints as a system level operation.

In the structure of the equations presented above is that the solution for the Lagrange multiplier vector, $\{\lambda\}$, requires the inversion of the matrix [A] in Eqn. (8). When there are many constraints being evaluated, the computational burden for solving Eqn. (8) tends to dominate the simulation run-time, because the computational burden associated with solving Eqn. (8) is proprotional to $O(N^3)$. Moreover, many of the matrix operations presented in Eqns. (1) through (5) are also proportional to $O(N^3)$, where N denotes the largest matrix dimension for some body. However, $N_c << N$ for large problems. The recursive $O(N)$ technique of the invention described below eliminates the need for simultaneuosly solving for all of the constraint loads via a single large algebraic equation.

By way of example, the formulation of the equations of motion for the instance of a particle, a rigid body and flexible body are illustrated below.

A). Particle Constraints

The mathematical models for constrained dynamics problems must account for the forces and torques required to maintain the kinematic constraint conditions defined by the user. Accordingly, in MD, position-dependent constraints are defined in the form:

$$C_j(R_1, \ldots R_{Np}) = a_j; j = 1, \ldots, N_c$$

where $C_j$ denotes the j-th constraint, $a_j$ denotes the constant or time-varying value of the constraint objective, and $N_c$ denotes the number of constraints. The functional form for the constraint permits arbitrary definitions for interrelationships between variables. Examples of potential types of constraints include: bond distance constraints, angle constraints, multipoint constraints, and rigid body constraints.

Because it is difficult to incorporate the position constraints directly into the EOM, the constraints are first differentiated with respect to time, yielding:

$$\sum_{r=1}^{N_P} \frac{\partial C_j}{\partial R_r} R_r = a_j$$

where $\partial(*)/\partial R_j$ denotes partial differentiation with respect to the j-th particle position vector and (') denotes differentiation with respect to time. When $\alpha$ is non-zero the constraints are time-varying and can be prescribed to satisfy arbitrary values (i.e., a non-holonomic rheonomic constraint). The EOM and constraint equation can be written as:

$$[m_j]\{R_j\} = \{F_j\} + [b_j]^T\{\Lambda\};$$

$$\sum_{\sigma=1}^{N_b} [b_\sigma]\{R_\sigma\} = \{A\};$$

$$[b_j]^T = [\nabla_j^T C_1, \ldots, \nabla_j^T C_{Nc}];$$

$$\{\Lambda\} = [\lambda_1, \ldots, \lambda_{Nc}]^T;$$

$$\{A\} = [a_1, \ldots a_{Nc}]^T$$

The analytic algebraic solution for $\Lambda$, can be shown to be:

$$\{\Lambda\} = \left( \sum_{\sigma=1}^{N_b} [b_\sigma][m_\sigma^{-1}][b_\sigma]^T \right)^{-1} \left\{ \{A\} - \sum_{\nu=1}^{N_b} ([b_\nu]\{R_\nu\} + [m_\nu^{-1}][b_\nu]\{F_\nu\}) \right\}$$

which is valid for both fixed and rheonomic constraints. It should be observed that the evaluation for $\{\Lambda\}$ is two time derivatives removed from the original definition for the position-dependent constraints. As a result, this formulation permits small numerical errors to accumulate during the integration of the EOM, because redundant DOF are retained in the physical model for the constrained MD system. To handle the induced constraint drift that arises in the integrated system response, a Reduced Variable Molecular Dynamics (RVMD) method, described below, can be used. This method completely eliminates the potential for induced drift in the integrated system response.

B). Rigid Body Constraints

For rigid bodies, the constraint equations are generalized as follows:

$$C_j(R_1, \theta_1, \ldots, R_n, \theta_N) = a_j; j = 1, \ldots, N_c$$

where $R_j$ denotes the j-th body reference point position vector locating the j-th body relative to inertial space;

$\theta_j$ denotes the vector of j-th body kinematic variables used for describing the orientation of the j-th body relative to the inertial frame. The constraint rates follows as:

$$\sum_{r=1}^{N} \frac{\partial C_j}{\partial R_r} R_r + \frac{\partial C_j}{\partial R_r} \theta_r = a_j; J = 1, \ldots, N_c$$

leading to constrained EOM of the form:

$$[m_j]\{A_j\} = \{F_j\} + [b_j]^T\{\Lambda\}$$

subject to $$\sum_{\alpha=1}^{N_b} [b_\sigma] \begin{Bmatrix} R_\sigma \\ \theta_\sigma \end{Bmatrix} = \{a_1, \ldots, a_{Nc}\}^T$$

where $$[b_\sigma] = [\nabla_{R1}, \nabla_{\theta1}, \ldots, \nabla_{RN}, \nabla_{\theta N}]_\sigma$$

$[m_j]$ denotes the 6×6 j-th body mass matrix, $F_j$ denotes the 6×1 j-th body force and torque vector, and $A_j = d^2(R_{xj}, R_{yj}, R_{zj}, \theta_{xj}, \theta_{yj}, \theta_{zj})/dt^2$ denotes the acceleration vector for the j-th body translation and orientation. The constraint matrix is generalized for both translational and rotational components. The solution for $\Lambda$ can be expressed in a functional form that is identical to the form obtained for the particle formulation.

C). Flexible Body Constraints

For flexible bodies the rigid body constraint equations are developed by adding the generalized Fourier series expansions used for describing the flexible body behavior. The flexible body response is described by coupled vector-valued sets of integro-partial differential equations. To simplify the solution process, the assumed flexible body displacement is described by a separation of variables technique. The spatial part of the solution is assumed to be provided by time-invariant eigenvector-like displacement shapes. The time-varying part of the solution is obtained by multiplying the spatial part of the assumed solution by time-varying amplitudes that measure the participation of the assumed displacement shapes in the instantaneous response. Typically the processed eigenvectors are obtained by first diagonalizing the Hessian matrix and then transforming the modes to account for nominal substructure interactions. Mathematically, the model for the flexible body response is defined by:

$$u(x,y,z,t) = \sum_{k=1}^{N_m} \phi_k(x,y,z)\eta_k(t)$$

where $\phi_k(*,*,*)$ denotes the processed k-th eigenvector, $\eta_k(*)$ denotes the k-th modal amplitude, and $N_m$ denotes the number of eigenvectors retained in the flexible body model. The flexible body constraints can be expressed as:

$$C_j(R_1, \theta_1, u_1, \ldots R_N, \theta_N, u_N) = a_j; j=1, \ldots, N_c$$

where $R_j$ denotes the j-th body reference point position vector locating the j-th body relative to inertial space; $\theta_j$ denotes the vector of j-th body kinematic variables used for describing the orientation of the j-th body relative to the inertial frame, and $u_j$ denotes the j-th flexible body deformation vector. The time derivative of the constraint equation yields:

$$\sum_{k=1}^{N_c} \frac{\partial C_j}{\partial R_k} R_k + \frac{\partial C_j}{\partial \theta_k} \theta_k + \frac{\partial C_j}{\partial \eta_k} \eta_k = a_j, j=1, \ldots N_c$$

The EOM for the flexible body case can be shown to be:

$$[m_j]\{A_j\} = \{F_j\} + [b_j]^T\{\Lambda\}$$

subject to $$\sum_{r=1}^{N_c} [b_\sigma] \{R_\sigma \theta_\sigma \eta_\sigma\}^T = \{a_1, \ldots, a_{N_c}\}^T$$

and $$[b_\sigma] = [\nabla_{R_1}, \nabla_{\theta_1}, \nabla_{\eta_1}, \ldots, \nabla_{R_n}, \nabla_{\theta_n}, \nabla_{\eta_n}]_\sigma$$

$[m_j]$ denotes the $(6+N_n) \times (6+N_n)$ j-th body mass matrix, $\{F_j\}$ denotes the $(6+N_n) \times 1$ body force, torque, and generalized modal force vector, and $\{A_j\} = d^2(R_{x_j}, R_{y_j}, R_{z_j}, \theta_{x_j}, \theta_{y_j}, \theta_{z_j}, \eta_{N_j} \ldots \eta_{N_j})/dt^2$ denotes the acceleration vector for the j-th body translation, orientation and body flexibility. The solution for $\{\Lambda\}$ is identical to the solution obtained for both the particle and rigid body formulations.

D). Multipole Expansions

In describing the dynamics of a molecule, it may be desirable to include force field calculations which can account for longe range body-body interactions, such as electrostatic interactions. To alleviate the $N^2$ energy evaluation effort required for non-bonded interactions, the long-range electrostatic field contribution can be computed via multipole expansions through 4-th order. The expansion for the potential is expressed as in FIG. 7. The potential and associated gradients are evaluated by introducing the generalized coordinates that describe the rigid body translation and rotation. The expressions have been found to be valid when the body separation distances are greater than 10Å. For separation distances less than 10Å, traditional particle interactions are computed. To complete the evaluation of the induced mechanical loads the approximate field expression must be used to evaluate the forces and torques that act on individual bodies. The resulting expressions are used to evaluate particle-rigid body as well as rigid body-rigid body interactions.

V. Recursive Generalized Coordinate Methodology

The modeling is divided into two parts: 1) the formulation and solution process for the EOM and 2) the development of mathematical models for the constraint functions to be supported by the RVMD method. The generation of EOM for interconnected systems defined by generalized coordinates uses the RVMD method with a recursive formulation having the following features: 1) the minimum set of independent DOF are retained in the EOM, 2) only small matrices are inverted, and 3) the solutions for the Lagrange Multipliers are obtained as the non-iterative solutions to low-order linear algebraic equations.

More particularly, the order N recursive method is structured to avoid the need to develop a full order system inertia matrix. Prior art multibody systems created full mass matrix or a large order mass matrix every integration step. Since inversion is an order $N^3$ operation, speed was severely effected. The MBO(N)D method of the present invention uses a recursion technique and relative coordinates. The recursion technique inverts body inertia matrices, but not the system inertia matrix. It also eliminates the need to solve a large order Lagrange Multiplier equation. The MBO(N)D method develops an inertia matrix for each body. It never inverts an inertia matrix greater than the number of velocity variables associated with the body. Thus, the subject O(N) recursive method greatly reduces the computational complexity involved in solving large order linear equations of the form $Ax=b$ by using noniterative recursive equations to generate the solution $x=A^{-1}b$. Table I gives an example of two ways of solving for the constraint forces between multiple rigid bodies. In this example, there are five constraints between each pair of bodies. The $O(N^3)$ algorithm inverts the $1745 \times 1745$ matrix in a single step. The O(N) algorithm locally solves for the constraint forces in a series of steps only requiring the inversion of $5 \times 5$ matrices. Thus the explicit equation that must be solved in a single step using a large matrix now is reduced to a series of implicit equations that are solved in many steps using small matrices. This comparison is shown in Table 1.

In an exemplary case, N bodies were linked together with each body having 6 degrees of freedom and 5 constraints between each body. For N=14, the recursive method of the invention was 1.9X faster than the generalized coordinate method. For N=350, the recursive method of the invention algorithm was 2523X faster.

TABLE 1

| $O(N^3)$ Methodology | O(N) Methodology |
| --- | --- |
| Solve $A\lambda = B$ | Solve $A_j\lambda_j = f(b_j, U_{j-1})(j = 2, \ldots, 350)$ |
| A = Constraint inertia matrix (1745 × 1745) | $A_j = j^{th}$ body constraint inertia matrix (5 × 5) |
| b = Joint Kinematics vector (1745 × 1) | $b_j = j^{th}$ joint kinematics vector (5 × 1) |
| $\lambda$ = Constrained joint degrees of freedom (DOF) loads (1745 × 1) | $\lambda_j = j^{th}$ body constrained joint degrees of freedom loads (5 × 1) |
| | $U_{j-1}$ = Inboard body acceleration |
| Comment: Explicit large-order symmetric equation solution | Comment: Implicit low-order symmetric equation solution |

The present invention provides an improved O(N) method for computing coupled system accelerations using the equations of motion obtained for a multibody system. Functionally, the O(N) method behaves as an efficient sparse matrix solution for implicit sets of differential equations. The major difference between $O(N^3)$ and O(N) algorithms is that small matrix computations replace large matrix computations. This is important because the computational effort required for evaluating matrix inversions is proportional to $O(\kappa)$, where $\kappa$ is the dimension of the matrix to be inverted. The sparse-matrix behavior of the O(N) method arises because of the combined effects of body-level processing and the multi-step nature of the approach. In the $O(N^3)$ methods all system level coupling effects are computed at one time. In contrast, the $O(N)$ methods invoke a multi-step process so that the system-level coupling effects can be evaluated via implicit sets of equations.

Figure 8:
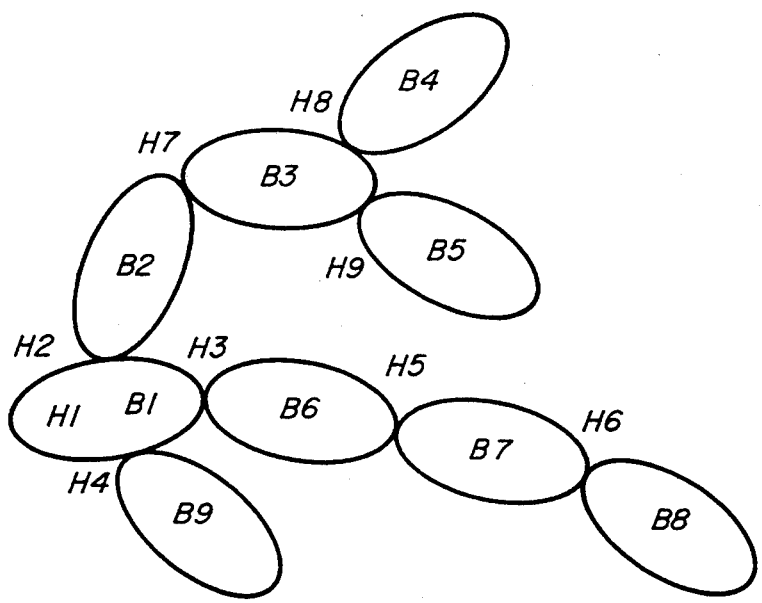
FIG. 8 is an example of a branched tree topology, where BX are bodies and HX are hinges.

In accordance with the present invention, a tree topology system such as the one presented in FIG. 8, is mapped onto the molecule system. The system is composed of rigid or flexible bodies. The base body is arbitrarily defined as Body 1. End bodies are defined as bodies (other than the base body) which have only one hinge connection. An end hinge is defined as the hinge associated with an end body. In FIG. 8, the end bodies are bodies 4, 5, 8, and 9, and the end hinges are hinges 8, 9, 6, and 4, respectively. A subscript i is used to identify a body which is currently under consideration. Those bodies relating to a body which is directly inboard (i.e., closer to the base body) are denoted by the subscript i−1. Bodies which are directly outboard (i.e., further from the base body) are denoted by a subscript i+1. These notational definitions do not imply any restrictions on the numbering sequence for the bodies. An end body is denoted by i=e, and the base body by i=1. Quantities relating to the hinge which is directly inboard of a body are denoted by subscript I, whereas those relating to a hinge which are directly outboard are denoted a subscript O. By definition there is only one hinge and body directly inboard of any given body, but there may be many hinges and bodies which may be directly outboard. The subscripts O and i+1 are used in a general context in these instances and do not denote any particular outboard hinge or body. The derivation assumes that the equations of motion have been obtained for each individual body and that the interconnection constraint conditions have been identified, leading to $$\text{Body } e: [M_e]\{U_e\} = \{G_e\} + [b_{Ie}^T][\phi_{Ie}]\{\lambda_{Ie}\} \quad (9)$$

$$\text{Body } i: [M_i]\{U_i\} = \{G_i\} + [b_{Ii}^T][\phi_{Ii}]\{\lambda_{Ii}\} + \left(\sum_O [b_{Oi}^T][\phi_{Oi}]\{\lambda_{Oi}\}\right) \quad (10)$$

for $i = 1, \ldots, e-1$ where $[b_{Ii}]$ and $[b_{Oi}]$ denote the kinematics coefficient matrix for the directly inboard hinge (subscript I) and directly outboard hinge (subscript O) of the i-th body, $[\lambda_{Ii}]$ and $[\lambda_{Oi}]$ denoted the $n_{ci} \times 1$ vectors of Lagrange multipliers associated with the fixed and rheonomic constraints at the directly inboard hinge (subscript I) and directly outboard hinge (subscript O) of the i-th body, $n_{ci}$ indicates the number of constraints, and $[\phi_{Ii}]$ and $[\phi_{Oi}]$ denote the $6 \times n_{ci}$ selection matrices of O's and I's which map the fixed and rheonomic constraints at the directly inboard hinge (subscript I) and directly outboard hinge (subscript O) of the i-th body into the appropriate hinge DOF. The matrix operators $[b_{Ii}]$ and $[b_{Oi}]$ act to transform the body velocity state to equivalent components resolved about the coordinate frames fixed in the hinge.

The kinematics equations of constraint are given by $$\text{Hinge 1: } [\phi_{I1}]\{\beta_{I1}^f\} + [\phi_{I1}]\{\alpha_{I1}\} = [b_{I1}]\{U_1\} \quad (11)$$

$$\text{Hinge } i: [\phi_{Ii}]\{\beta_{Ii}^f\} + [\phi_{Ii}]\{\alpha_{Ii}\} = [b_{O,i-1}]\{U_{i-1}\} + [b_{Ii}]\{U_i\} \quad (12)$$

for $i = 2, \ldots, e$ where $[\phi_{Ii}]$ is a selection matrix for the free hinge DOF, and the following kinematical conditions hold for the free and constrained hinge selection matrices:

$$[\phi_{Ii}^T][\phi_{Ii}] = I_f, \ [\phi_{Ii}^T][\phi_{Ii}] = I_c, \ [\phi_{Ii}^T][\phi_{Ii}] = 0,$$
$$[\phi_{Ii}] = [\phi_{O,i-1}]$$

where $I_f$ represents an $n_f \times n_f$ identify matrix, $n_f$ is number of free DOF for the i-th hinge, and $I_c$ represents an $n_{ci} \times n_{ci}$ identity matrix.

A). Implicit Equations for the End Body Acceleration

The solution for the end body acceleration state requires that the user deal with two unknowns. The first unknown is the Langrange multiplier, $\{\lambda_{Ie}\}$, which defines interaction constraint loads between the (e-1)-th and e-th bodies. The second unknown is the e-th body acceleration. In the classical $O(N^3)$ approach the Lagrange multipliers are computed simultaneously throughout the multibody system via Eqn. (8). The recursive algorithm presented here creates implicit sets of equations for the transformed equations of motion and the hinge Lagrange Multipliers. The equations of motion are mapped to a space of minimum dimension. In the lower dimensional space the constrained DOF are analytically eliminated. A byproduct of this operation is that fewer equations must be integrated and the numerical errors arising from integrating redundant DOF are not present. The calculation for the Lagrange Multipliers now require matrix problems with the dimension of the constrained DOF for each hinge. This change dramatically impacts the computational burden associated with evaluating the Lagrange Multipliers when compared with the operations requires for solving Eqn, (8).

One key step in the development of the recursive form of the acceleration calculations follows on defining a kinematic expression relating velocity and acceleration components of bodies connected through a hinge. The first step in the process consists of differentiating the hinge kinematics equation defined by Eqn. (12), leading to equation (13) below $$[\phi_{Ii}]\{\dot{\beta}_{Ie}^f\}$$
$$+[\phi_{Ie}]\{\alpha_{Ie}\} = [b_{O,e-1}]\{\dot{U}_{e-1}\}$$
$$+[b_{Ie}]\{\dot{U}_e\}$$
$$+[\dot{b}_{O,e-1}]\{U_{e-1}\}$$
$$+[\dot{b}_{Ie}]\{U_e\}$$

where the "f" in $\{\beta_{Ie}^f\}$ denotes free hinge degrees of freedom, structure of the $[b^{**}]$ matrices depend on the model assumed for the body. A unique solution for $\{U_e\}$ is obtained by factoring the $[b_{Ie}]$ matrix as follows:

$$[b_{Ie}] \triangleq \begin{matrix} [R_{Ie} & | & F_{Ie}] \\ (6 \times 6) & & (6 \times n_e) \end{matrix}$$

where $[R_{Ie}]$ represents the rigid body part of the transformation matrix $[F_{Ie}]$ represents the flexible body part of the transformation matrix, and $n_e$ represents the number of deformation modes for the end body. The desired solution for $\{U_e\}$ follows as $$\{U_e\} = \quad (14)$$

$$\left\{\begin{array}{c}\gamma_e\\ \xi_e\end{array}\right\} = [\psi_e]\left\{\begin{array}{c}\beta_{Ie}^f\\ \xi_e\end{array}\right\} + \left\{\begin{array}{c}[R_{Ie}^{-1}](\{\zeta_e\} - [b_{O,e-1}]\{U_{e-1}\})\\ 0\end{array}\right\}$$

where $$[\psi_e] = \left\{\begin{array}{cc}[R_{Ii}^{-1}][\phi_{Ii}] & -[R_{Ii}^{-1}][F_{Ii}]\\ 0 & 1\end{array}\right\}.$$

$$\{\zeta_i\} = [\phi_{Ii}]\{\alpha_{Ii}\} - [b_{O,i-1}]\{U_{i-1}\} - [b_{Ii}]\{U_i\}$$

It should be noted that the subscript e in Eqns. (13) and (14) can be replaced by the subscript i, since the kinematics for the end hinge is the same as for an intermediate hinge.

Equation (14) represents a kinematical coordinate transformation which relates the e-th body acceleration state to the (e-1)-th body acceleration plus the free hinge DOF acceleration state.

The end body equation of motion is transformed into recursive form by introducing Eqn. (14) into Eqn. (9), leading to $$[M_e][\psi_e]\left\{\begin{array}{c}\beta_e^f\\ \xi_e\end{array}\right\} = \{G_e\} + [b_{Ie}^T][\phi_{Ie}]\{\lambda_{Ie}\} -$$

$$[M_e]\left\{\begin{array}{c}[R_{Ie}^{-1}](\{\zeta_e\} - [b_{O,e-1}]\{U_{ej-1}\})\\ 0\end{array}\right\}$$

Pre-multiplying the equation above by $[\Psi_e^T]$, one obtains the transformed equation of motion:

$$\left\{\begin{array}{c}\beta_e^f\\ \xi_e\end{array}\right\} = \quad (15)$$

$$[M_e^{-1}][\psi_e^T]\left(\{G_e\} - [M_e]\left\{\begin{array}{c}[R_{Ie}^{-1}](\{\zeta_e\} - [b_{O,e-1}]\{U_{e-1}\})\\ 0\end{array}\right\}\right)$$

where
$$[M_e] = [\psi_e^T][M_e][\psi_e]$$

A key step in Eqn. (15) is that the matrix product, $[e^T][b_{Ie}^T][\phi_e]$, multiplying $\{\lambda_{Ie}\}$ can be shown to be identically zero because of the orthogonality of the $[\phi_{Ie}]$ and $[\phi_{Ie}]$ selection matrices. Equation (15) is implicit because the acceleration vector $\{U_{e-1}\}$ appears in the equation and can only be evaluated when the inboard body acceleration is known. The solution process for establishing the implicit body acceleration equations is presented in Sections V.(B) through Section V.(C).

B). Implicit Equation for the Outboard Body Lagrange Multiplier

Though the Lagrange Multiplier, $\{\lambda_{Ie}\}$, has been eliminated from the implicit acceleration equation presented in Eqn. (15), this vector of interconnection constraint loads still appears in the acceleration equation for $\{U_{e-1}\}$ and must either be computed or eliminated from the inboard body equation of motion. An algebraic equation for the Lagrange Multiplier, $\{\lambda_{Ie}\}$, is obtained by first solving Eqn. (9) for $\{U_e\}$, leading to $$\{U_e\} = [M_e^{-1}](\{G_e\} + [b_{Ie}^T][\phi_{Ie}]\{\lambda_{Ie}\}) \quad (16)$$

Introducing Eqn. (16) into Eqn. (13) provides an algebraic equation which can be solved for the Lagrange Multiplier, yielding $$\{\lambda_e\} = [J_e][\phi_{Ie}^T](\{\zeta_e\} - [b_{Ie}][M_e^{-1}]\{G_e\} - [b_{O,e-1}]\{U_{e-1}\}) \quad (17)$$

where $$[J_e] = ([\phi_{Ie}^T][b_{Ie}][M_e^{-1}][b_{Ie}^T][\phi_{Ie}])^{-1}$$

Equations (15) and (17) are implicit because of the appearance of the term $\{U_{e-1}\}$. The solution for $\{\lambda_{Ie}\}$ is analogous to the procedure used in Eqns. (6), (7) and (8) for solving for the system-level Lagrange Multiplier, $\{\lambda\}$.

The structure of the transformed equations of motion and the Lagrange Multiplier solution represent generic forms for the recursive structure of the O(N) method. A proof by induction for the general i-th element of a tree topology structure is presented below.

C). Transformed Dynamics Equation for an Intermediate Body

A proof by induction for a generic body depends on assuming a solution for the Lagrange Multiplier, $\{\lambda_{Oi}\}$, of the form:

$$\{\lambda_{Oi}\} = [J_{i+1}][\phi_{I,i+1}^T](\{\zeta_{i+1}\} - [b_{I,i+1}] [M_{i+1}^{-1}]\{G_{i+1}\} - [b_{Oi}]\{U_i\}) \quad (18)$$

and carrying out the recursive transformation for the next inboard body. If the solution for the inboard Lagrange Multiplier has the same form as the assumed solution for the outboard Lagrange Multiplier, the general solution has been established by induction. Introducing Eqn. (18) into the i-th equation of motion leads to $$[M_i]\{U_i\} = \{G_i\} + b_{Ii}^T[\phi_{Ii}]\{\lambda_{Ii}\} \quad (19)$$

where $$[M_i] = [M_{i}] + \epsilon_0[b_{Oi}^T][\phi_{I,i+1}][J_{i+1}][\phi_{I,i+1}^T][b_{Oi}]$$
$$\{G_i\} = \{M_i\} + \epsilon_0[b_{Oi}^T][\phi_{I,i+1}][J_{i+1}][\phi_{I,i+1}^T]$$
$$(\{\zeta_{i+1}\} - [b_{I,i+1}][M_{i+1}^{-1}]\{G_{i+1}\})$$

$[M_i]$ represents a generalized mass matrix which accounts for the i-th body and all of the bodies outboard of it, and $\{Gi\}$ represents a generalized force vector which accounts for the loads acting on the i-th body and all of the bodies outboard of it. It can be anticipated that $[M_i]$ and $\{G_i\}$ should be directly useful for designing control commands to achieve design objectives. Because the functional form of Eqn. (19) is identical to Eqn. (9), the transformed equation of motion and Lagrange Multiplier solution can be written as $$\left\{\begin{array}{c}\beta_{Ii}^f\\ \xi_i\end{array}\right\} = [M_i^{-1}][\psi_i^T]\left\{\begin{array}{c}[R_{Ii}^{-1}](\{\zeta_i\} - [b_{O,i-1}]\{U_{i-1}\})\\ 0\end{array}\right\} \quad (20)$$

where

-continued
$$[M_i] = [\psi_i^T][M_i][\psi_i]$$

similar manipulations lead to $$\{\lambda_{Ii}\} = [J_i][\phi_{Ii}^T]$$
$$(\{\zeta_i\} - [b_{Ii}][M_i^{-1}]\{G_i\} - [b_{o,i-1}]\{U_{i-1}\}) \quad (21)$$

where $$[J_i] = ([\phi_{Ii}^T][b_{Ii}][M_i^{-1}][b_{Ii}^T][\phi_{Ii}])^{-1} \quad 10$$

On observing the Eqns. (18) and (21) have identical functional forms, it follows that the recursive equations have been established by induction.

D). Transformed Dynamics Equation for the Base Body

The only body requiring special attention is the base body, because the hinge kinematic constraint vector from Eqn. (11), repeated here, is functionally dependent on the base body velocity state:

$$[\phi_{I1}]\{\beta_{I1}^f\} + [\phi_{I1}]\{\alpha_{I1}\} = [b_{I1}]\{U_1\}$$

If we assign the inertial frame velocity vector, $\{U_0\}$, to be identically zero, from Eqn. (20) the transformed base body equation of motion can be written as $$\begin{Bmatrix} \beta_{I1}^f \\ \xi_1 \end{Bmatrix} = [M_1^{-1}][\psi_1^T]\left(\{G_1\} - \begin{Bmatrix} [R_{I1}^{-1}]\{\zeta_1\} \\ 0 \end{Bmatrix}\right)$$

where $$\{\zeta_1\} = [\phi]\{\alpha_1\} - [b_{I1}]\{U_1\}$$

On observing that no Lagrange Multipliers or unknown implicit velocity states appear in Eqn. (22), it follows that Eqn. (22) can be uniquely solved for the base body accelerations. The next phase of the method seeks to recursively generate the implicitly defined variables in the acceleration equations. Using the coordinate transformation defined by Eqn. (14) when i=1, $\{U_i\}$ can computed and is required in the implicitly defined equation for Eqn. (20) when i=2. A repeated application of Eqns. (14) and (20) then recursively provide the unknown inboard body accelerations defined on the backward sweep.

The O(N) method requires that a three-part sweeping process be carried out for generating numerical values for the constrained system accelerations. The first sweep defines the absolute velocity states for each of the bodies from either initial conditions or previously integrated state positions and velocities. The second sweep generates the implicit equation for the equations of motion and the hinge Lagrange Multipliers. The third sweep solves the base body equation of motion and recursively generates the implicit acceleration states required for computing the transformed equations of motion defined in the second sweep.

E). First Sweep Solution Process

On the first forward sweep, the 6 absolute rate coordinates (including absolute angular and linear velocity components) associated with each body are developed as functions of the coordinates used to define hinge rate, modal rate and the absolute rate of the inboard body. The pass starts with body 1 and proceeds outward to the end of each branch. The state variables, $\{\beta_{If}\}$, $\}\beta_{If}\}$, $\{\zeta_j\}$, $\{\zeta_j\}$ for j=1, ..., $N_b$ are assumed to have been specified. User specific hinge constraint time histories are assumed to have been specified for $\{\alpha\}$, $\{\alpha\}$, and $\{\alpha\}$. The computational sequences for the first sweep follows as For the base body, i=1, compute the following:

$$\{\gamma_1\} = [R_{I1}^{-1}]([\phi_{I1}]\{\beta_{I1}^f\} + [\phi_{I1}]\{\alpha_{I1}\} - [F_{I1}]\{\xi_1\})$$

$$\{U_1\} = \begin{Bmatrix} \lambda_1 \\ \xi_1 \end{Bmatrix}$$

$$\{\zeta_1\} = [\phi_{I1}]\{\alpha_{I1}\} - [b_{I1}]\{U_1\}$$

$$[\psi_1] = \begin{bmatrix} [R_{I1}^{-1}][\phi_{I1}] & - [R_{I1}^{-1}][F_{I1}] \\ 0 & I \end{bmatrix}$$

The $[F_{I1}]\{\zeta_1\}$ term has been included in the theoretical development of these equations, but it should be recognized as null for the base body. By definition, the g-frame hinge point 1 is aligned with the body fixed reference and there is no modal displacement measured at this point. If there actually is modal displacement of the grid point coincident with the reference point, it can be utilized as a sensor point so that its deformation can be monitored relative to the reference frame coordinates.

For all other bodies, the recursion proceeds outboard from body 1 in accordance with the tree topolgy. For i=2, ..., e, compute:

$$\{\gamma_i\} = [R_{Ii}^{-1}]([\phi_{Ii}]\{\beta_{Ii}^f\} + [\phi_{Ii}]\{\alpha_{Ii}\} - [F_{Ii}]\{\xi_i\})$$

$$\{U_i\} = \begin{Bmatrix} \lambda_i \\ \xi_i \end{Bmatrix}$$

$$\{\zeta_i\} = [\phi_{Ii}]\{\alpha_{Ii}\} - [b_{Ii}]\{U_i\}$$

$$[\psi_i] = \begin{bmatrix} [R_{Ii}^{-1}][\phi_{Ii}] & - [R_{Ii}^{-1}][F_{Ii}] \\ 0 & I \end{bmatrix}$$

F). Backward Sweep for Transformed Forces and Masses

The first forward sweep has generated all of the kinematic variables that are required for defining the equations of motion. The backward sweep recursively generates the transformed equations of motion in terms of a minimum set of DOF and recursively computes the equivalent inertia and equivalent generalized force vectors which account for all outboard bodies. To obtain the desired acceleration expression for an end body, the kinetics equation of an end body, body e, is defined as $$[M_e]\{U_e\} = \{G_e\} + [b_{Ie}^T][\phi_{Ie}]\{\lambda_{Ie}\} \quad (23)$$

The desired acceleration expression for the kinetics equation of an intermediate body, body i, i=1,2, ..., e−1 is defined as $$[M_i]\{\dot{U}_i\} = \{G_i\} + [b_{ii}^T][\phi_{ii}]\{\lambda_{Ii}\} + \sum_o [b_{oi}^T][\phi_{oi}]\{\lambda_{oi}\} \quad (24)$$

The summation over o is carried out over all of the directly outboard hinges.

As set out above, the solution for the end body acceleration state requires that two unknowns be dealt with. The first is the Lagrange multiplier $\{\lambda_{Ie}\}$ which defines interaction constraint loads between bodies $e-1$ and $e$. The second unknown is the e-th body acceleration. The recursive routine presented herein creates implicit sets of equations for the transformed equations of motion and hinge Lagrange multipliers. A key step in the development of the recursive form of the acceleration calculations is in defining a kinematic expression relating velocity and acceleration components of bodies connected through a hinge, and is accomplished by differentiating the hinge kinematic equation. The recursive process starts with the outboard e-th body and progresses to the base body as follows:

For $i=1,\ldots,e$, Initialize:

$$[M_i] = [M_i]$$

$$\{G_i\} = \{G_i\}$$

Compute:

$$[M] = [\Psi_e][M_{ee}^{T-1}][\Psi_e]$$

For $i=e,\ldots,2$, Compute:
Temporary Variables:

$$A_1] = [M_i^{-1}][b_{ii}^T][\phi_{ii}]$$

$$[A_2] = ([\phi_{ii}][b_{ii}][A_1])^{-1}[\phi_{ii}][b_{o,i-1}]$$

Accumulation:

$$[M_{i-1}] := [M_{i-1}] + [b_{o,i-1}^T][\phi_{ii}][A_2]$$
$$\{G_{i-1}\} := \{G_{i-1}\} + [A_w^T]\{[\phi_{ii}]\{\zeta_i\} - [A_1^T]\{G_i\}\}[$$
$$M_i] = [\Psi_i^T][M_i][\Psi_i]$$

H). Second Forward Pass for the Implicit Acceleration Equations

The second forward pass solves the transformed base body equation of motion and generates the implicit vectors required for solving the second outboard body equation of motion. This process is used to recursively generate the unknowns required in the implicit equations of motion defined in the backward sweep. The second forward sweep begins with the base body and terminate with the end body or bodies. The required computations follow as For $i=1$, Compute:

$$\begin{Bmatrix} \beta_{ii}^f \\ \xi_1 \end{Bmatrix} = [M_1^{-1}][\psi_1^T]\left(\{G_1\} - [M_1]\begin{pmatrix} [R_{II}^{-1}]\{\zeta_1\} \\ 0 \end{pmatrix}\right)$$

$$\{\gamma_1\} = [R_{II}^{-1}]([\phi_{II}]\{\beta_{II}^f\} + \{\zeta_1\} - [F_{II}]\{\xi_1\})$$

$$\{U_1\} = \begin{Bmatrix} \gamma_1 \\ \xi_1 \end{Bmatrix}$$

For $i=2,\ldots,e$, Compute:

$$\begin{Bmatrix} \beta_{ii}^f \\ \xi_1 \end{Bmatrix} =$$

$$[M_1^{-1}][\psi_1^T]\left(\{G_1\} - [M_1]\begin{pmatrix} [R_{II}^{-1}]\{\zeta_i\} - [b_{o,i-1}]\{U_{i-1}\} \\ 0 \end{pmatrix}\right)$$

$$\{\gamma_i\} = [R_{II}^{-1}]([\phi_{II}]\{\beta_{II}^f\} + \{\zeta_i\} - [b_{o,i-1}]\{U_{i-1}\} - [F_{II}]\{\xi_i\})$$

$$\{U_1\} = \begin{Bmatrix} \gamma_1 \\ \xi_1 \end{Bmatrix}$$

When comparing the manipulations required to generate Eqn. (8) and Eqn. (18), the recursive solution process appears cumbersome. However, it is important to observe that the dimension of the matrices that have to be inverted to generate the algebraic solutions for the Lagrange Multipliers is very different for these two approaches. For example, the matrix to be inverted in Eqn. (8) can be of very high dimension (i.e., ranging from tens to thousands for large problems). Alternatively, the dimension of matrices to be inverted in Eqn. (18) can be no larger than $(6+n)$, where n is the number of flexible DOF for the body. The potentially large difference in matrix dimension for the Lagrange multiplier vector, because the computational effort for inverting matrices is proportional to the cube of the matrix dimension.

VI. Applications

Figure 9:
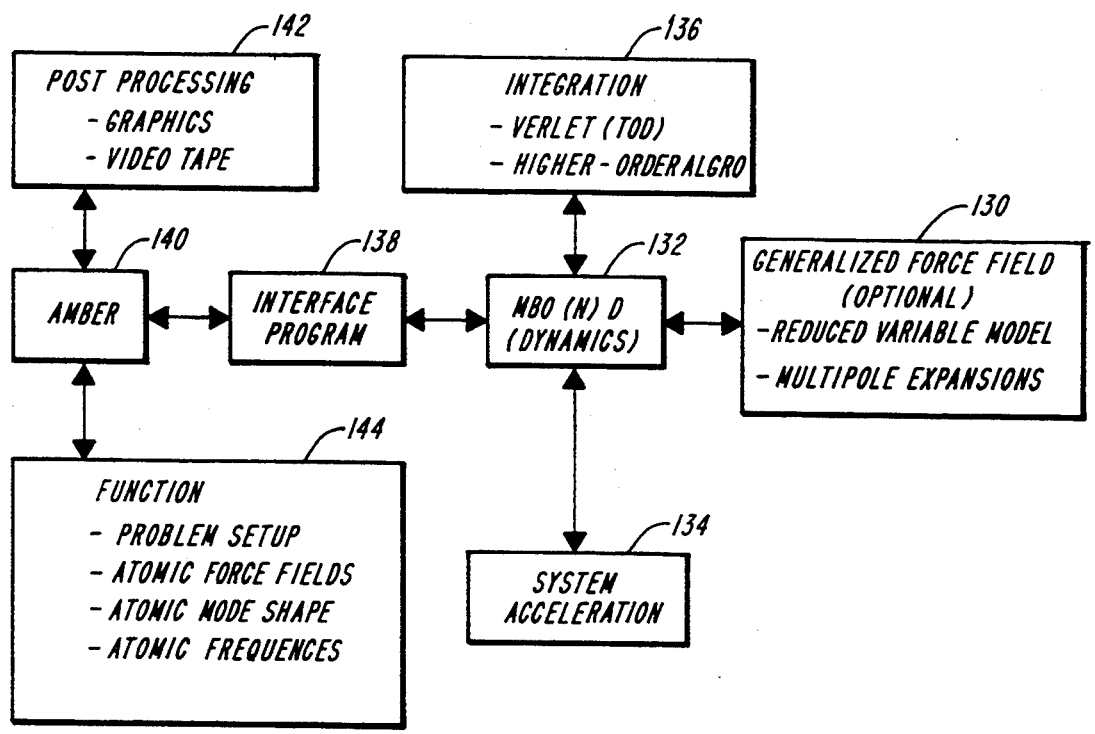
FIG. 9 is a block diagram showing an exemplary method of the invention.

The following applications illustrate some of the capabilities of the variable reduction simulation program. All of the applications were carried out using a combined version of AMBER and MBO(N)D (AMBER-AM[3]). As shown in FIG. 9, the software packages are connected by interface modules. The modular structure allows information to easily pass between the two programs. AMBER handles all of the molecular system setup, force field calculation, and analysis. MBO(N)D handles all of the details of the dynamics simulation, as well as all coordinate conversions. With only minor modifications, any arbitrary force field may be substituted for the AMBER force field.

A. Bond Constraints

The first example involves a short 4 ps simulation on glycine dipeptide. The results of an AMBER simulation using the SHAKE algorithm to constrain bond lengths and an AMBER-MBO(N)D simulation using exact bond constraints are compared. The later program uses the recursive generalized variable algorithm with a distance constraint of the form $$\rho_{ij} = |R_i - R_j| - d_{ij}$$

defined for the i-th and j-th bonded atoms. FIG. 10 summarizes the results of the two simulations. The results of a 4 ps Amber simulation using SHAKE with a 0.5 and 1 fs step size and a Verlet integration algorithm were compared with a 4 ps AMBER—MBO(N)D simulation using a 1 and 2 fs time step and a 4th order Runge-Kutta integration scheme. The average values for total energy, as well as Phi and Psi are given. The RMS fluctuations are given in parenthesis below the average values.

The initial Amber velocities were obtained from a random Boltzmann distribution calculated at 300° K. The MBO(N)D velocities were corrected to eliminate components along the bonds. Since the initial conditions are slightly different, one cannot expect the trajectories to be identical.

Figure 11A:
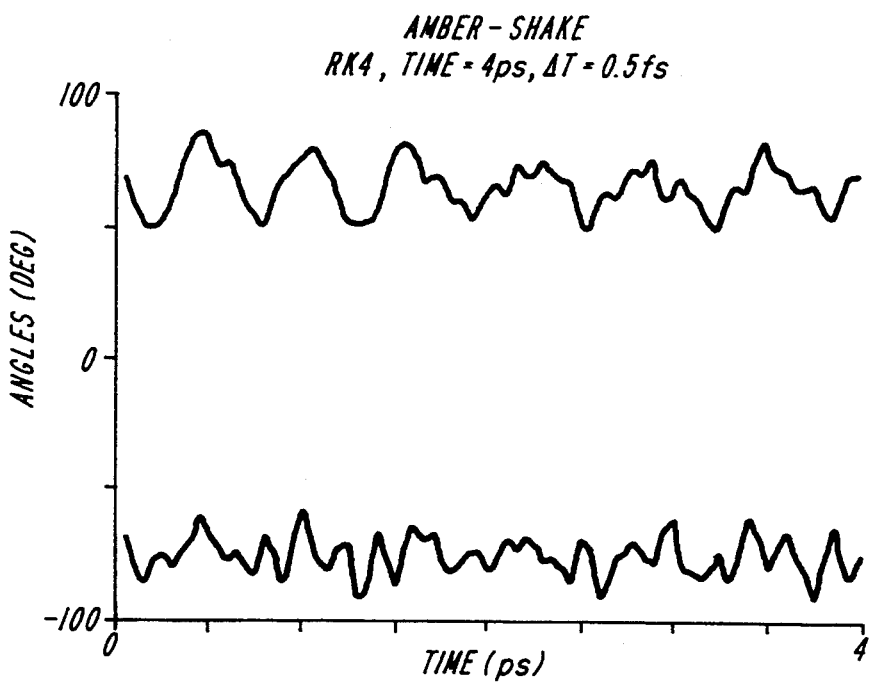
FIGS. 11A AND 11B show the Phi and Psi dihedral angles as a function of the trajectory step calculated from two dynamics simulations on a glycine dipeptide using AMBER and MBO(N)D respectively.
Figure 11B:
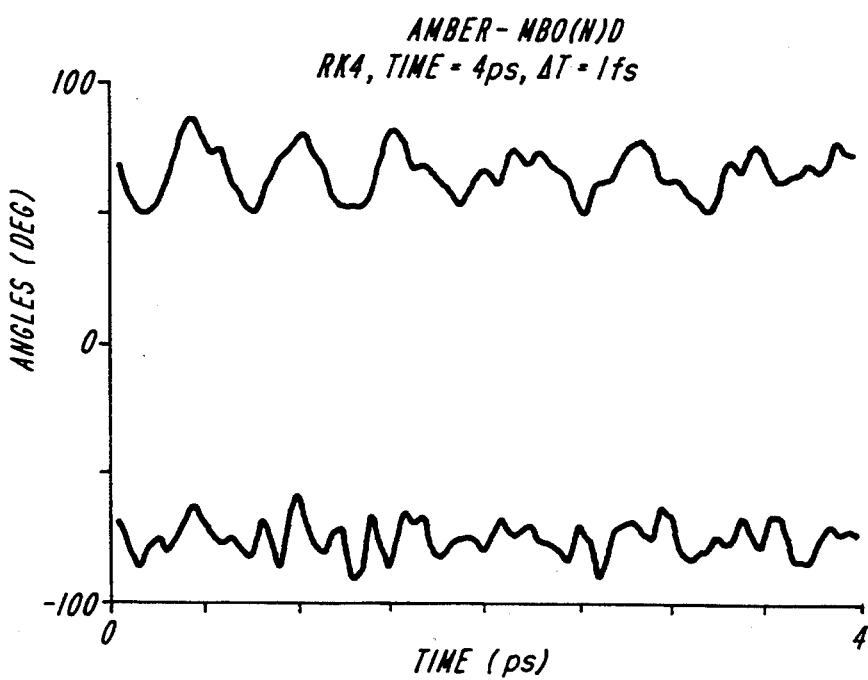

The total energy was well conserved on the MBO(N)D simulation and in fact was a order of magnitude better than that of the Amber-SHAKE run. The values of Phi and Psi dihedral angles as a function of the trajectory step are given in FIGS. 11A and 11B. They are almost identical in the two simulations over the 4 ps time interval. Toward the end of the 4 ps, they began to diverge. The results of this investigation demonstrate that the MBO(N)D method can be succesfully linked with molecular modeling software. Evaluating the results of this MBO(N)D simulation suggests its performance is in excellent agreement with dynamics calculations made using a SHAKE simulation.

B. Flexible Constraints

The alpha helical conformation of decaglycine (73 atoms) was minimized by Amber and the normal modes were computed. This structure was heated up to 300° K. over a 5 ps period and then 20 ps of dynamics were carried out using SHAKE bond constraints. The Verlet integrator was used with a 1 fs step size. After the simulation, the RMS deviation of every atom from its average position in the simulation was computed.

Figure 12:
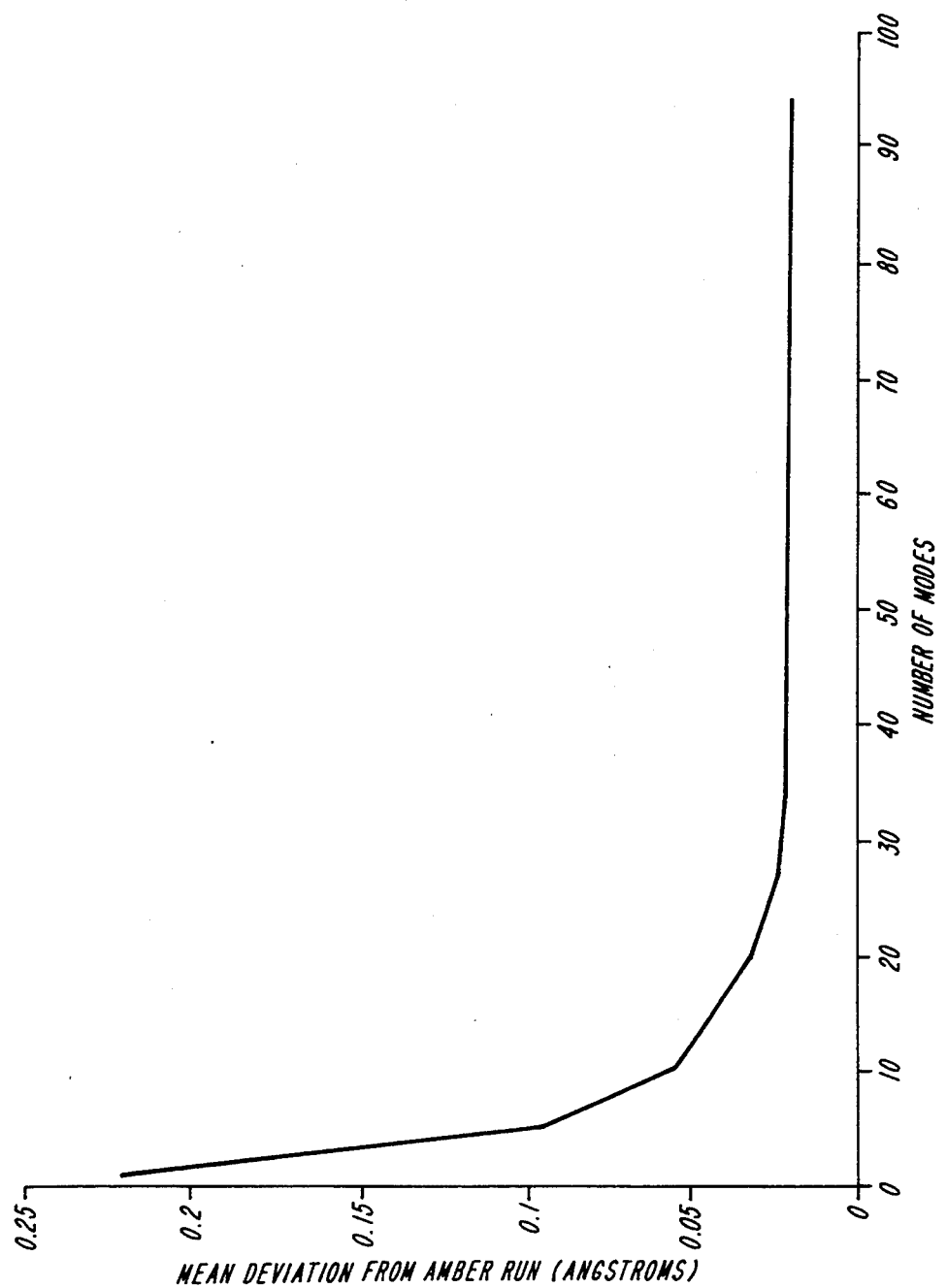
FIG. 12 shows the mean deviation, relative to an AMBER simulation, of each MBO(N)D dynamics simulation run performed on decaglycine, with different combinations of vibrational Modes.

MBO(N)D was used to carry out 20 ps simulation runs based on various combinations of Amber modes calculated at the minimized geometry. The simulations were also run with different step sizes. The RMS deviation of all atoms from their equilibrium positions was then computed and compared with the results from the Amber run. FIG. 12 shows the mean deviation of each MBO(N)D run with the AMBER simulation.

The amplitude of each mode was calculated to contribute a time-averaged potential energy of $(\frac{1}{2})k_BT$, leading to $$a_k = \frac{\sqrt{2k_BT}}{\omega_k}$$

where $k_B$ is Boltzmann's constant, T is the absolute temperature, and $\omega_k$ is the modal frequency.

The 20 mode model appears to be the best choice for reproducing the results of the AMBER simulation. All modes below 75 cm$^{-1}$ have been retained in this model. FIG. 13 shows the result of varying the maximum step size. Even a step size as large as 80 fs gives good agreement with the AMBER run. However, when one also requires the RMS deviation of the total energy to be less than 10%, the 32 fs step size is best. At this step size, the total simulation time is approximately 10X faster than the AMBER simulation time and produces similar quantitative results.

C. Multibody Constraints

To test the program's ability to successfully describe the motion of a molecule with multiple segments, a helical fragment (237 atoms) was selected from the crystal structure of bacteriorhodopsin. This helix has a PRO residue in the middle of a 25 residue sequence. Since the presence of the PRO residue disrupts the helical H-bond network, bending motion between the helical segments above and below the PRO is possible.

Figure 14:
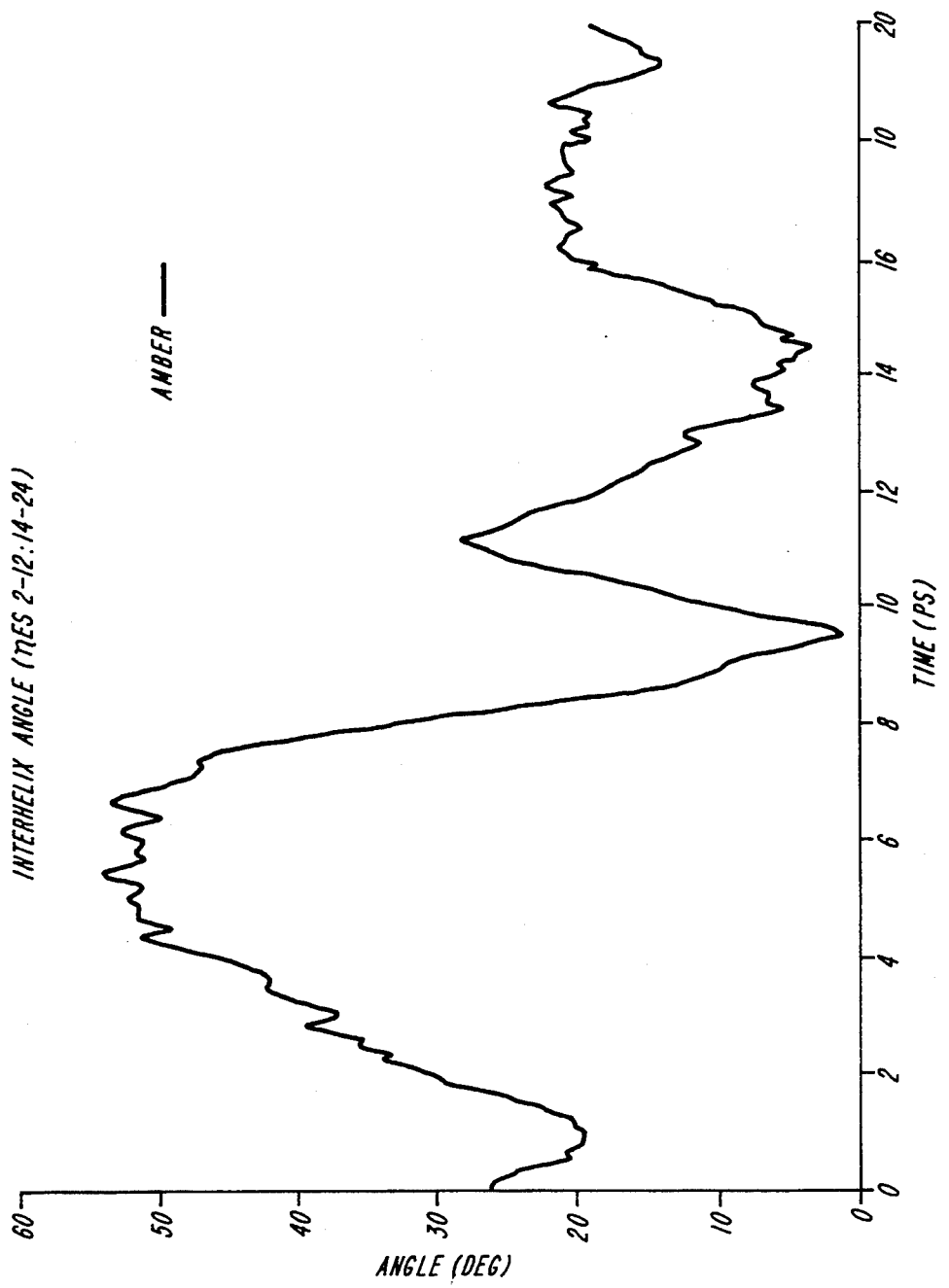
FIG. 14 shows the motion by way of the the top and bottom helical segments of a fragment of bacteriorhodpsin over a 20 ps simulation performed by SHAKE at 300° K.

The nearest energy minimum was located and the fragment was then heated up to 300° K. A 20 ps simulation was then carried out using only SHAKE bond constraints. The angle between the top and bottom helical segments was monitored by measuring the angle between the best least squares lines fit to each helical segment. FIG. 14 shows that very large scale motion occurs on a 10 ps time scale.

Figure 15:
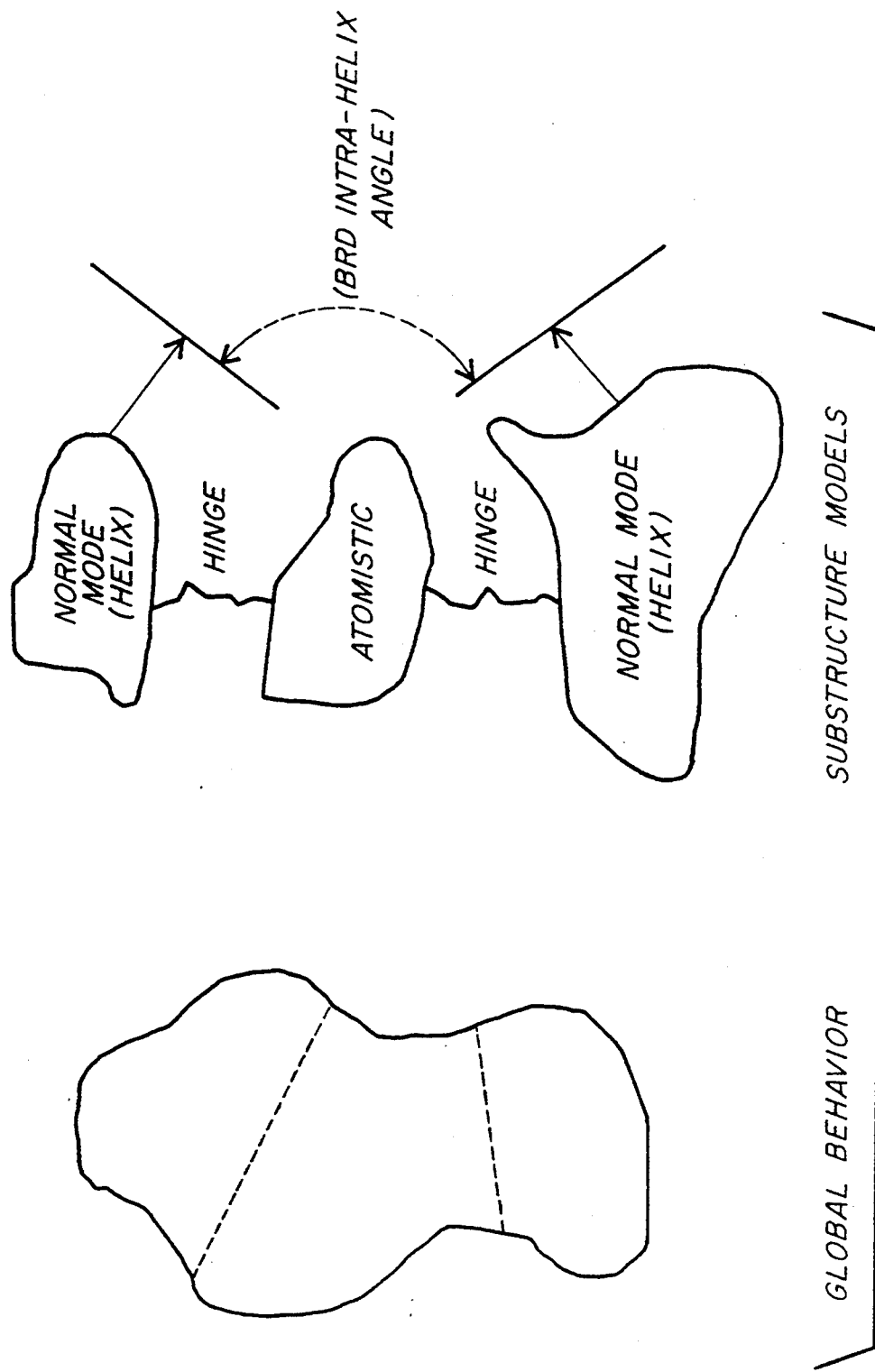
FIG. 15 is an exemplary model of rigid and flexible bodies for MBO(N)D simulation of a fragment of bacteriorhodopsin.

MBO(N)D simulations were then carried out using different combinations of rigid and flexible bodies, as shown in FIG. 15. Each flexible body must have a set of modes that describe its motion. These modes are calculated from the initially determined minimum energy structure using the conventional normal mode calculation.

FIG. 16 shows that the RMS fluctuations of the angle between the 2 helix lobes is sensitive to the type of flexibility assigned to each body. The number in parenthesis represents the number of modes used for the flexible bodies. "Particle" denotes a completely flexible PRO residue.

The central PRO must be able to undergo a dihedral transition in order for the large motion of the end lobes to occur. A modal model for this fragment does not allow this transition to occur. It is also important that the end lobes have at least a minimal amount of modal motion in order for the proper amount of motion in the end segments to occur. These were only the results of a single run, however. We are currently investigating the results of multiple runs averaged to see if similar results are obtained. It should be noted that trying each of these different models was very straightforward and that the AMBER software did not have to be modified other than requesting the type of constraints desired.

D. Multipole Expansion

Figure 17:
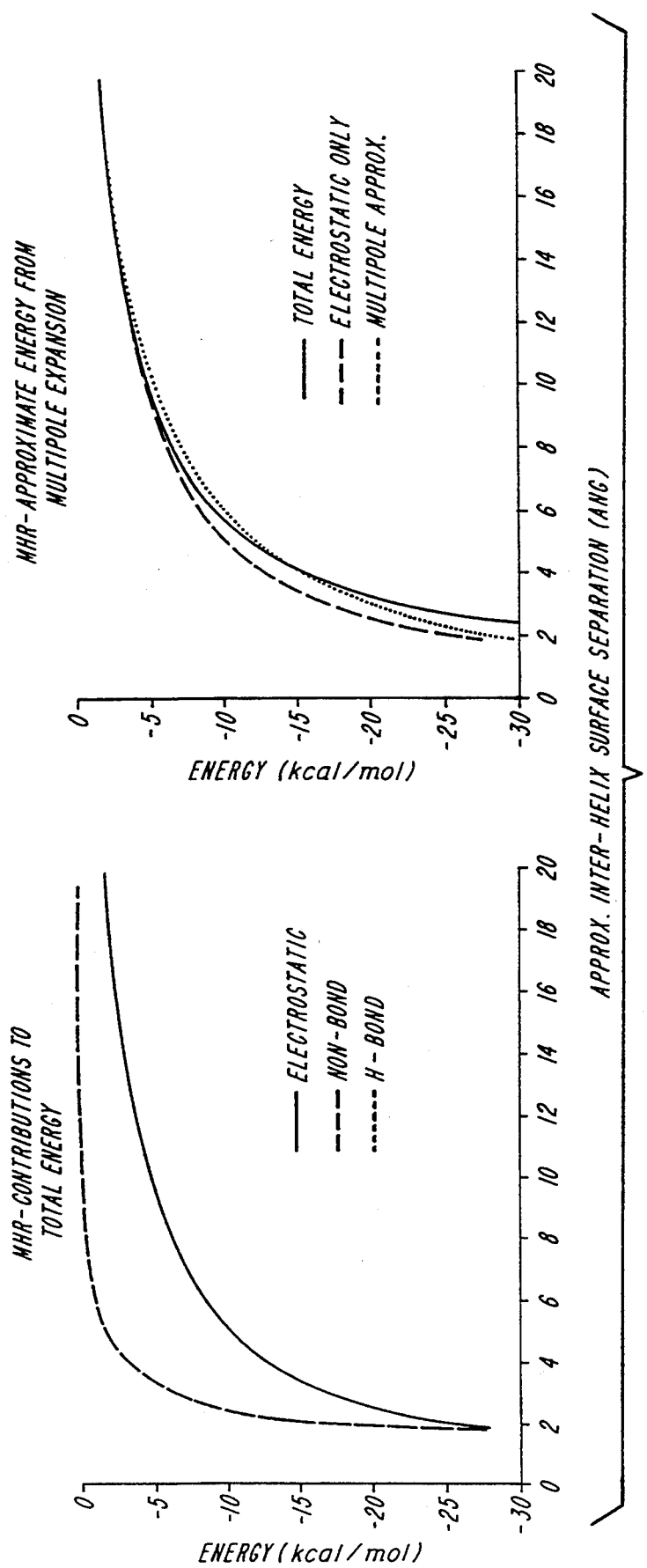
FIG. 17 shows the energy components calculated by AMBER and by multipole expansion methods for two helices of myohemerythrin.

Tests of the multipole expansion were carried out on two helices of myohemerythrin (346 atoms). The helices were pulled apart, as rigid bodies, from their equilibrium position along the axis perpendicular to the helix axes. At each point, both the total non-bonded AMBER energy and the helix-helix interaction energy using a 4-th order multipole expansion were computed. FIG. 17 shows that above 10A only the AMBER electrostatic component makes a significant contribution to the total nonbonded energy and that the multipole expansion is a very good approximation.

Figure 18:
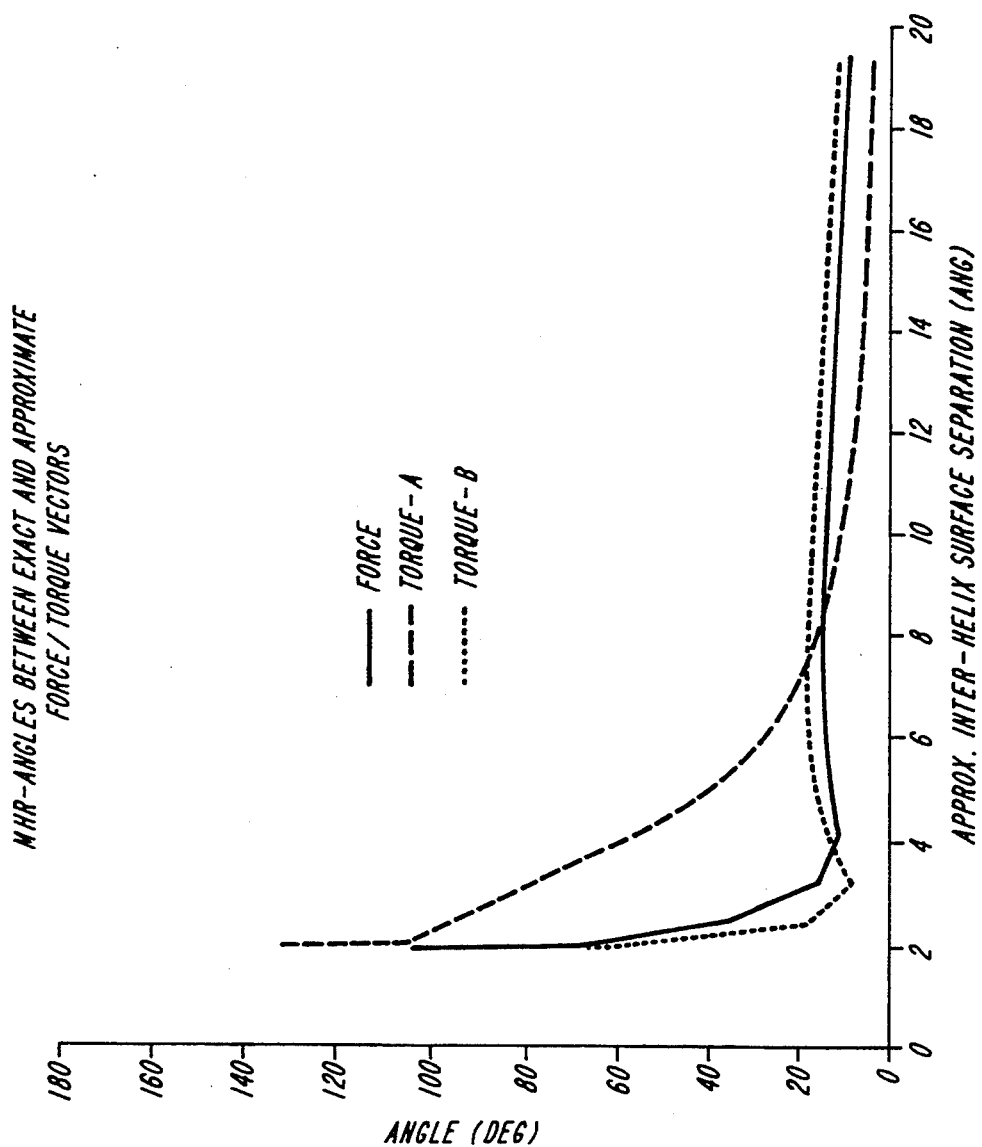
FIG. 18 compares the exact force between two helices of myohemerythrin as calculated by AMBER, with the approximate force and torque vectors calculated by multipole expansion.

FIG. 18 shows that the approximate force and torque vectors on the two helices is within 5°–10° of the exact values computed from the original AMBER force field. The use of a multipole expansion for computing helix-helix interactions reduced the force field computational time by a factor of 44.

The preferred form of the method of the present invention can be implemented on a Silicon Graphics 4D/210 computer, with a IRIX 4.05 operating system.

The invention may be embodied in other specific forms without departing from the spirit of essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A computer-assisted method for generating a dynamic model of a molecule, said molecule including a predetermined set of atoms in a predetermined atomic structure, comprising the steps of:
   A. providing information representative of said atomic structure, and
   B. generating model data for said molecule, said model, data defining
      i. rigid bodies corresponding to groups of one or more of said atoms of said molecule characterized by substantially no relative movement therebetween,
      ii. flexible bodies corresponding to groups of two or more atoms of said molecule characterized by relative movement therebetween, and
      iii. flexure elements, each of said flexure elements defining an interconnection of two of said rigid bodies and said flexible bodies, said interconnection having predetermined degrees of freedom.

2. The method of claim 1, comprising the further steps of:
   C. generating first base data representative of position coordinates and velocities of the atoms of said molecule measured with respect to a reference coordinate system,
   D. generating second base data for each flexible body representative of body deformation motions of said flexible body,
   E. processing said first base data, said second base data, and said model data, including the substeps of:
      i. for each of said rigid bodies:
         a. identifying a body coordinate system for said rigid body,
         b. determining for each atom in said rigid body the position, velocity and acceleration measured with respect to said body coordinate system,
      ii. for each of said flexible bodies:
         a. identifying a body coordinate system for said flexible body,
         b. determining for each atom in said flexible body with position, velocity and acceleration measured with respect to said body coordinate system,
         c. determining for said flexible body at least one modal amplitude and modal rate associated with said flexible body,
      iii. defining hinge constraints between adjacent ones of said rigid bodies and said flexible bodies, said hinge constraints being defined with respect to said body coordinate systems of said adjacent ones of said bodies, and said hinge constrains defining a components of a vector $\{\beta\}$ representative of generalized coordinates of all of said bodies,
      iv. determining from said generalized coordinates, hinge rates corresponding to $$\frac{d}{dt}\{\beta\}(=\{\dot{\beta}\})$$

and hinge accelerations corresponding to $$\frac{d}{dt}\{\dot{\beta}\}(=\{\ddot{\beta}\})$$

v. determining an equation of motion for each of said rigid bodies and said flexible bodies, said equations of motion defining a vector $\{U_i\}$, where i is an index representative of said bodies, and
      vi. recursively determining from $\{U_i\}$ the absolute position and velocity of each of said bodies.

3. The method of claim 2 wherein at least one of said rigid bodies corresponds to a single atom.

4. The method of claim 2, wherein the equation of motion for each of said bodies is determined in accordance with one from a group consisting of the LaGrange Method, and the Newton-Euler method.

5. The method of claim 2, wherein the hinge constraint between two of said adjacent bodies is defined at substantially adjacent points of said adjacent bodies.

6. The method of claim 2, wherein $(\beta)$ varies with time.

7. The method of claim 2, wherein $(\beta)$ does not vary with time.

8. The method of claim 7, wherein said vector $(\beta)$ is equal to zero.

9. The method of claim 2 wherein said recursive determining step includes the sub-step of implementing an O(N) procedure.

10. The method of claim 2 wherein the equation of motion is of the form:

$$U = [M]^{-1}[G + B\lambda]$$

where U is representative of the absolute acceleration of said body, [M] is representative of the mass of said body, G is representative of the generalized force vector for said body, B is representative of the constraint kinematic coefficient matrix for said body, and $\lambda$ is a Lagrange multiplier for the hinge constraints of said body.

11. The method of claim 10 wherein said recursive determining step includes the substeps of:
   (1) defining a tree topology for said bodies,
   (2) defining one of said bodies as a base body,
      said base body having a component of vector $(\beta)$ associated therewith in relation to inertial space, and one or more components of vector $(\beta)$ associated with bodies adjacent to said base body in said tree topology, and
      wherein said other bodies are intermediate bodies in said tree topology when having components of vector $(\beta)$ associated with itself and at least two other bodies, and
      wherein said other bodies are end bodies in said tree topology when having a component of vector associated with itself and only one other body,
   (3) determining the absolute rate $r_o$ of said base body with respect to inertial space,
   (4) starting with said base body and progressing serially on said tree topology outward along said intermediate bodies to said end bodies, determining absolute rate associated with each of said intermediate bodies and said end bodies, said absolute rate for each body being determined from the hinge rate, modal rate and absolute rate of the next inboard body on said tree topology,
   (5) starting with said end bodies and progressing serially on said tree topology inward along said intermediate bodies to said base body, determining equivalent inertia and equivalent generalized forces associated with each of said bodies, said equivalent inertia and said equivalent generalized forces for each of said bodies being determined from the equivalent inertia the equivalent generalized forces of the next outboard body on said tree topology, (6) starting with said base body and progressing serially on said tree topology outward along said intermediate bodies to said end bodies, determining the relative hinge accelerations and modal accelerations for each of said bodies, said relative hinge acceleration and said relative modal acceleration for each body being determined from the relative hinge acceleration and modal acceleration of the next inboard body on said tree topology.

12. The method of claim 11 wherein said substep (6) includes for each body, the substep of:

solving for $\lambda$ from said equations of motion, and solving said equations of motion for $\{U_i\}$.

13. The method of claim 12 wherein said solving substep includes the substep of performing numerical integration with an integration step $\Delta t$.

14. The method of claim 13 wherein said integration step $\Delta t$ is a predetermined value.

15. The method of claim 13 wherein said integration step $\Delta t$ is an adaptively determined value.

16. The method of claim 10, wherein said recursive determining step includes the sub-step of implementing an O(N) procedure.

17. The method of claim 10, wherein at least one of said rigid bodies corresponds to a single atom.

18. A computer-assisted method for generating a dynamic model of a molecule, said molecule including a predetermined set of atoms in a predetermined atomic structure, comprising the steps of:

A. generating model data for said molecule, said model data defining
   i. bodies corresponding to groups of one or more of said atoms of said molecule, and
   ii. flexure elements, each of said flexure elements defining an interconnection of two of said bodies, said interconnection having predetermined degrees of freedom, B. generating first base data representative of position coordinates and velocities of the atoms of said molecule measured with respect to a reference coordinate system, C. processing said first base data and said model data including the substeps of:
   i. for each of said bodies:
      a. identifying a body coordinate system for said body,
      b. determining for each atom in said body the position, velocity and acceleration measured with respect to said body coordinate system,
   ii. defining hinge constraints between adjacent ones of said bodies, said hinge constraints being defined with respect to said body coordinate systems of said adjacent ones of said bodies, and said hinge constraints defining a component of a vector $\{\beta\}$ representative of generalized coordinates of all of said bodies,
   iii. determining from said generalized coordinates, hinge rates corresponding to $$\frac{d}{dt}\{\beta\}(=\{\dot{\beta}\})$$

and hinge accelerations corresponding to $$\frac{d}{dt}\{\dot{\beta}\}(=\{\ddot{\beta}\})$$

iv. determining an equation of motion for each of said bodies, said equations of motion defining a vector $\{U_i\}$, where i is an index representative of said bodies, and
   v. recursively determining from $[U_i]$ the absolute position and velocity of each of said bodies.

19. The method of claim 18, wherein the equation of motion for each of said bodies is derived from equations of motion solved to describe acceleration, velocity and positional coordinates over time for said molecule.

20. The method of claim 18, wherein the equation of motion for each of said bodies is determined in accordance with one from a group consisting of the LaGrange method and the Newton-Euler method.

21. The method of claim 18 wherein said recursive determining step includes the sub-step of implementing an O(N) procedure.

22. The method of claim 18 wherein the equation of motion is of the form:

$$U=[M]^{-1}[G+B\lambda]$$

where U is representative of the absolute acceleration of said body, is representative of the mass of said body, G is representative of the generalized force vector for said body, B is representative of a constraint kinematic coefficient matrix for said body, and $\lambda$ is a Lagrange multiplier for said hinge constraints of said body.

23. The method of claim 18, wherein said body coordinate system for each of said bodies is a local coordinate system which moves with said body.

24. The method of claim 18, wherein said body coordinate system for each of said bodies is an inertial coordinate system.

25. The method of claim 18 wherein said recursive determining step includes the substeps of:

(1) defining a tree topology for said bodies,
(2) defining one of said bodies as a base body,
    said base body having a component of vector ($\beta$) associated therewith in relation to inertial space, and one or more components of vector till associated with bodies adjacent to said base body in said tree topology, and
    wherein said other bodies are intermediate bodies in said tree topology when having components of vector $\{\beta\}$ associated with itself and at least two other bodies, and
    wherein said other bodies are end bodies in said tree topology when having a component of vector $\{\beta\}$ associated with itself and only one other body,
(3) determining the absolute rate $r_o$ of said base body with respect to inertial space,
(4) pursuant to a first forward sweep starting with said base body and progressing serially on said tree topology outward along said intermediate bodies to said end bodies, determining an absolute rate associated with each of said intermediate bodies and said end bodies, said absolute rate for each body being determined from the hinge rate, and absolute rate of the next inboard body on said tree topology, (5) pursuant to a backward sweep starting with said end bodies and progressing serially on said tree topology inward along said intermediate bodies to said base body, recursively generating implicit equations of motion and hinge Lagrange multipliers associated with each of said bodies, (6) pursuant to a second forward sweep starting with said base body and progressing serially on said tree topology outward along said intermediate bodies to said end bodies, solving the equation of motion of said base body and recursively generating implicit acceleration states necessary for solving said implicit equations of motion of each of said intermediate bodies and said end bodies.

26. The method of claim 25, wherein recursively generating said implicit equations of motion and said hinge Lagrange multipliers in said backward sweep comprises determining equivalent inertia and equivalent generalized forces associated with each of said bodies, said equivalent inertia and said equivalent generalized forces for each of said bodies being determined from the equivalent inertia and the equivalent generalized forces of the next outboard body on said tree topology, 27. The method of claim 26, wherein recursively generating said implicit acceleration states in said second forward sweep comprises determining relative hinge accelerations and modal accelerations for each of said bodies, said relative hinge acceleration and said modal acceleration for each body being determined from the relative hinge acceleration and modal acceleration of the next inboard body on said tree topology.

28. The method according to claim 26, comprising the further steps of:
   i. generating said model data in terms of rigid bodies corresponding to groups of one or more of said atoms of said molecule characterized by substantially no relative movement therebetween, and flexible bodies corresponding to groups of two or more atoms of said molecule characterized by relative movement therebetween,
   ii. generating second base data for each flexible body representative of body deformation motions of said flexible body, and
   iii. determining for said flexible body at least one modal amplitude and modal rate associated with said flexible body, wherein said position, velocity and acceleration measured with respect to said body coordinate system is determined by processing said first base data, said second base data, and said model data, and said absolute rate determined in said first forward sweep is determined from said hinge rate, said modal rate and said absolute rate of the next inboard body on said tree topology.

29. The method of claim 18, wherein said bodies defined by said model data further comprise rigid bodies corresponding to groups of one or more of said atoms of said molecule characterized by substantially no relative movement therebetween, and flexible bodies corresponding to groups of two or more atoms of said molecule characterized by relative movement therebetween.

30. The method of claim 29, further comprising
   i. generating second base data for each flexible body representative of body deformation motions of said flexible body, and
   ii. determining for said flexible body at least one modal amplitude and modal rate associated with said flexible body, wherein said position, velocity and acceleration measured with respect to said body coordinate system is determined by processing said first base data, said second base data, and said model data.

31. The method of claim 30 wherein the equation of motion is of the form:

$$U=[M]^{-1}[G+B\lambda]$$

where U is representative of the absolute acceleration of said body, is representative of the mass of said body, G is representative of the generalized force vector for said body, B is representative of the constraint kinematic coefficient matrix for said body, and $\lambda$ is a Lagrange multiplier for the hinge constraints of said body.

32. The method of claim 31 wherein said recursive determining step includes the sub-step of implementing an O(N) procedure.

33. The method of claim 31 wherein said recursive determining step includes the substeps of:
   (1) defining a tree topology for said bodies,
   (2) defining one of said bodies as a base body,
      said base body having a component of vector ($\beta$) associated therewith in relation to inertial space, and one or more components of vector ($\beta$) associated with bodies adjacent to said base body in said tree topology, and
      wherein said other bodies are intermediate bodies in said tree topology when having components of vector ($\beta$) associated with itself and at least two other bodies, and
      wherein said other bodies are end bodies in said tree topology when having a component of vector $[\beta]$ associated with itself and only one other body,
   (3) determining the absolute rate $r_o$ of said base body with respect to inertial space,
   (4) starting with said base body and progressing serially on said tree topology outward along said intermediate bodies to said end bodies, determining absolute rate associated with each of said intermediate bodies and said end bodies, said absolute rate for each body being determined from the hinge rate, modal rate and absolute rate of the next inboard body on said tree topology,
   (5) starting with said end bodies and progressing serially on said tree topology inward along said intermediate bodies to said base body, determining equivalent inertia and equivalent generalized forces associated with each of said bodies, said equivalent inertia and said equivalent generalized forces for each of said bodies being determined from the equivalent inertia and the equivalent generalized forces of the next outboard body on said tree topology,
   (6) starting with said base body and progressing serially on said tree topology outward along said intermediate bodies to said end bodies, determining the relative hinge accelerations and modal accelerations for each of said bodies, said relative hinge acceleration and said modal acceleration for each body being determined from the relative hinge acceleration and modal acceleration of the next inboard body on said tree topology.

34. The method of claim 31 wherein at least one of said rigid bodies corresponds to a single atom.

35. The method of claim 31 wherein said substep (6) includes for each body, the substep of solving for $\lambda$ from said equations of motion, and solving said equations of motion $\{U_i\}$.

36. The method of claim 35 wherein said solving substep includes the substep of performing numerical integration with an integration step $\Delta t$.

37. The method of claim 36 wherein said integration step $\Delta t$ is a predetermined value.

38. The method of claim 36 wherein said integration step $\Delta t$ is an adaptively determined value.

39. A computer system for generating a dynamic model of a molecule, said molecule including a predetermined set of atoms in a predetermined atomic structure, comprising:
A. means for providing information representative of said atomic structure, and
B. model data means for generating model data for said molecule, said model data defining
   i. rigid bodies corresponding to groups of one or more of said atoms of said molecule characterized by substantially no relative movement therebetween,
   ii. flexible bodies corresponding to groups of two or more atoms of said molecule characterized by relative movement therebetween, and
   iii. flexure elements, each of said flexure elements defining an interconnection of two of said rigid bodies and said flexible bodies, said interconnection having predetermined degrees of freedom.

40. The system of claim 39, further comprising the further steps of:
C. first base data means for generating first base data representative of position coordinates and velocities of the atoms of said molecule measured with respect to a reference coordinate system,
D. second base data means for generating second base data for each flexible body representative of body deformation motions of said flexible body,
E. processor means for processing said first base data, said second base data, and said model data, including the substeps of:
   i. for each of said rigid bodies:
      a. identifying a body coordinate system for said rigid body,
      b. determining for each atom in said rigid body the position, velocity and acceleration measured with respect to said body coordinate system,
   ii. for each of said flexible bodies:
      a. identifying a body coordinate system for said flexible body,
      b. determining for each atom in said flexible body the position, velocity and acceleration measured with respect to said body coordinate system,
      c. determining for said flexible body at least one modal amplitude and modal rate associated with said flexible body,
   iii. defining hinge constraints between adjacent ones of said rigid bodies and said flexible bodies, said hinge constraints being defined with respect to said body coordinate systems of said adjacent ones of said bodies, and said hinge constraints defining a component of a vector $\{\beta\}$ representative of generalized coordinates of all of said bodies,
   iv. determining from said generalized coordinates, hinge rates corresponding to $$\frac{d}{dt}\{\beta\}(=\{\dot{\beta}\})$$

and hinge accelerations corresponding $$\frac{d}{dt}\{\dot{\beta}\}(=\{\ddot{\beta}\})$$

v. determining an equation of motion for each of said rigid bodies said flexible bodies, said equations of motion defining a vector $\{U_i\}$, where i is an index representative of said bodies, and
   vi. recursively determining from $\{U_i\}$ the absolute position and velocity of each of said bodies.

41. The system of claim 40 wherein said processor means recursively determines the absolute position and velocity of each of said bodies by implementing an O(N) procedure.

42. The method of claim 40, wherein at least one of said rigid bodies corresponds to a single atom.

43. The system of claim 40 wherein said processor means determines said equation of motion in the form:

$$U=[M]^{-1}[G+B\lambda]$$

where U is representative of the absolute acceleration of said body, is representative of the mass of said body, G is representative of the generalized force vector for said body, B is representative of the constraint kinematic coefficient matrix for said body, and $\lambda$ is a Lagrange multiplier for the hinge constraints of said body.

44. The system of claim 43 wherein said processor means recursively determines the absolute position and velocity of each of said bodies by implementing the substeps of:
(1) defining a tree topology for said bodies,
(2) defining one of said bodies as a base body, said base body having a component of vector ($\beta$) associated therewith in relation to inertial space, and one or more components of vector $\{\beta\}$ associated with bodies adjacent to said base body in said tree topology, and
   wherein said other bodies are intermediate bodies in said tree topology when having components of vector $\{\beta\}$ associated with itself and at least two other bodies, and
   wherein said other bodies are end bodies in said tree topology when having a component of vector $\{\beta\}$ associated with itself and only one other body,
(3) determining the absolute rate $r_o$ of said base body with respect to inertial space,
(4) starting with said base body and progressing serially on said tree topology outward along said intermediate bodies to said end bodies, determining absolute rate associated with each of said intermediate bodies and said end bodies, said absolute rate for each body being determined from the hinge rate, modal rate and absolute rate of the next inboard body on said tree topology,
(5) starting with said end bodies and progressing serially on said tree topology inward along said intermediate bodies to said base body, determining equivalent inertia and equivalent generalized forces associated with each of said bodies, said equivalent inertia and said equivalent generalized forces for each of said bodies being determined from the equivalent inertia and the equivalent generalized forces of the next outboard body on said tree topology, (6) starting with said base body and progressing serially on said tree topology outward along said intermediate bodies to said end bodies, determining the relative hinge accelerations and modal accelerations for each of said bodies, said relative hinge acceleration and said relative modal acceleration for each body being determined from the relative hinge acceleration and modal acceleration of the next inboard body on said tree topology.

45. A new computer system for generating a dynamic model of a molecule, said molecule including a predetermined set of atoms in a predetermined atomic structure, comprising:
A. means for providing information representative of said atomic structure, and
B. model data means for generating model data for said molecule, said model data defining
  i. bodies corresponding to groups of one or more of said atoms of said molecule, and
  ii. flexure elements, each of said flexure elements defining an interconnection of two of said bodies, said interconnection having predetermined degrees of freedom,
B. first base data means for generating first base data representative of position coordinates and velocities of the atoms of said molecule measured with respect to a reference coordinate system,
C. processor means for processing said first base data and said model data including the substeps of:
  i. for each of said bodies:
    a. identifying a body coordinate system for said body,
    b. determining for each atom in said body the position, velocity and acceleration measured with respect to said body coordinate system,
  ii. defining hinge constraints between adjacent ones of said bodies, said hinge constraints being defined with respect to said body coordinate systems of said adjacent ones of said bodies, said hinge constraints defining a component of a vector $\{\beta\}$ representative of generalized coordinates of all of said bodies,
  iii. determining from said generalized coordinates, hinge rates corresponding to $$\frac{d}{dt}\{\beta\}(=\{\dot\beta\})$$

and
hinge accelerations corresponding to $$\frac{d}{dt}\{\dot\beta\}(=\{\ddot\beta\})$$

iv. determining an equation of motion for each of said bodies, said equation of motion defining a vector $\{U_i\}$, where i is an index representative of said bodies, and
  v. recursively determining from $\{U_i\}$ the absolute position and velocity of each of said bodies.

46. The system of claim 45 wherein said processor means recursively determines the absolute position and velocity of each of said bodies by implementing an O(N) procedure.

47. The system of claim 45, wherein said body coordinate system identified for each of said bodies by said processor means is a local coordinate system which moves with said body.

48. The system of claim 45, wherein said body coordinate system identified for each of said bodies by said processor means is an inertial coordinate system.

49. The system of claim 45, wherein said bodies defined by said model data means are further defined as rigid bodies corresponding to groups of one or more of said atoms of said molecule characterized by substantially no relative movement therebetween, and flexible bodies corresponding to groups of two or more atoms of said molecule characterized by relative movement therebetween.

50. The system of claim 49, further comprising second base data means for
  i. generating second base data for each flexible body representative of body deformation motions of said flexible body, and
  ii. determining for said flexible body at least one modal amplitude and modal rate associated with said flexible body,
wherein said position, velocity and acceleration measured with respect to said body coordinate system is determined by processing said first base data, said second base data, and said model data.

51. The system of claim 50 wherein said processor means determines said equation of motion is of the form:

$$U=[M]^{-1}[G+B\lambda]$$

where U is representative of the absolute acceleration of said body, is representative of the mass of said body, G is representative of the generalized force vector for said body, B is representative of the constraint kinematic coefficient matrix for said body, and $\lambda$ is a Lagrange multiplier for the hinge constraints of said body.

52. The system of claim 51 wherein said processor means recursively determines the absolute position and velocity of each of said bodies by implementing the substeps of:
  (1) defining a tree topology for said bodies,
  (2) defining one of said bodies as a base body, said base body having a component of vector $\{\beta\}$ associated therewith in relation to inertial space, and one or more components of vector $\{\beta\}$ associated with bodies adjacent to said base body in said tree topology, and
    wherein said other bodies are intermediate bodies in said tree topology when having components of vector $\{\beta\}$ associated with itself and at least two other bodies, and
    wherein said other bodies are end bodies in said tree topology when having a component of vector $\{\beta\}$ associated with itself and only one other body,
  (3) determining the absolute rate $r_o$ of said base body with respect to inertial space,
  (4) starting with said base body and progressing serially on said tree topology outward along said intermediate bodies to said end bodies, determining absolute rate associated with each of said intermediate bodies and said end bodies, said absolute rate for each body being determined from the hinge rate, modal rate and absolute rate of the next inboard body on said tree topology, (5) starting with said end bodies and progressing serially on said tree topology inward along said intermediate bodies to said base body, determining equivalent inertia and equivalent generalized forces associated with each of said bodies, said equivalent inertia and said equivalent generalized forces for each of said bodies being determined from the equivalent inertia and the equivalent generalized forces of the next outboard body on said tree topology, (6) starting with said base body and progressing serially on said tree topology outward along said intermediate bodies to said end bodies, determining the relative hinge accelerations and modal accelerations for each of said bodies, said relative hinge acceleration and said modal acceleration for each body being determined from the relative hinge acceleration and modal acceleration of the next inboard body on said tree topology.

53. The system of claim 45, wherein said processor means recursively determines the absolute position and velocity of each of said bodies by implementing the substeps of:

(1) defining a tree topology for said bodies, (2) defining one of said bodies as a base body, said base body having a component of vector $\{\beta\}$ associated therewith in relation to inertial space, and one or more components of vector $\{\beta\}$ associated with bodies adjacent to said base body in said tree topology, and
    wherein said other bodies are intermediate bodies in said tree topology when having components of vector $\{\beta\}$ associated with itself and at least two other bodies, and
    wherein said other bodies are end bodies in said tree topology when having a component of vector $\{\beta\}$ associated with itself and only one other body, (3) determining the absolute rate to of said base body with respect to inertial space, (4) pusuant to a first forward sweep starting with said base body and progressing serially on said tree topology outward along said intermediate bodies to said end bodies, determining an absolute rate associated with each of said intermediate bodies and said end bodies, said absolute rate for each body being determined from the hinge rate, and absolute rate of the next inboard body on said tree topology, (5) pursuant to a backward sweep starting with said end bodies and progressing serially on said tree topology inward along said intermediate bodies to said base body, recursively generating implicit equations of motion and hinge Lagrange multipliers associated with each of said bodies, (6) pursuant to a second forward sweep starting with said base body and progressing serially on said tree topology outward along said intermediate bodies to said end bodies, solving the equation of motion of said base body and recursively generating implicit acceleration states necessary for solving said implicit equations of motion of each of said intermediate bodies and said end bodies.

54. The system of claim 53, wherein recursively generating said implicit equations of motion and said hinge Lagrange multipliers in said backward sweep comprises determining equivalent inertia and equivalent generalized forces associated with each of said bodies, said equivalent inertia and said equivalent generalized forces for each of said bodies being determined from the equivalent inertia and the equivalent generalized forces of the next outboard body on said tree topology.

55. The system of claim 53, wherein recursively generating said implicit acceleration states in said second forward sweep comprises determining relative hinge accelerations and modal accelerations for each of said bodies, said relative hinge acceleration and said modal acceleration for each body being determined from the relative hinge acceleration and modal acceleration of the next inboard body on said tree topology.

56. The system according to claim 53, wherein said bodies defined by said model data means are further defined in terms of rigid bodies corresponding to groups of one or more of said atoms of said molecule characterized by substantially no relative movement therebetween, and flexible bodies corresponding to groups of two or more atoms of said molecule characterized by relative movement therebetween, the system further comprising second base data means for a. generating second base data for each flexible body representative of body deformation motions of said flexible body, and b. determining for said flexible body at least one modal amplitude and modal rate associated with said flexible body, wherein said position, velocity and acceleration measured with respect to said body coordinate system is determined by processing said first base data, said second base data, and said model data, and said absolute rate determined in said first forward sweep is determined from said hinge rate, said modal rate and said absolute rate of the next inboard body on said tree topology.

* * * * *